United States Patent
Bamdad et al.

(10) Patent No.: US 12,115,192 B2
(45) Date of Patent: Oct. 15, 2024

(54) **CHIMERIC ANTIGEN RECEPTOR COMPOSITIONS AND METHODS FOR TREATING MUC1* DISEASES**

(71) Applicant: Minerva Biotechnologies Corporation, Waltham, MA (US)

(72) Inventors: Cynthia Bamdad, Boston, MA (US); Benoit Smagghe, Honolulu, HI (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 18/429,758

(22) Filed: Feb. 1, 2024

(65) Prior Publication Data

US 2024/0261331 A1    Aug. 8, 2024

Related U.S. Application Data

(60) Provisional application No. 63/482,972, filed on Feb. 2, 2023.

(51) Int. Cl.
| | | |
|---|---|---|
| *A61K 35/17* | (2015.01) | |
| *A61K 39/00* | (2006.01) | |
| *A61P 35/00* | (2006.01) | |
| *C07K 16/30* | (2006.01) | |

(52) U.S. Cl.
CPC .......... *A61K 35/17* (2013.01); *A61K 39/4611* (2023.05); *A61K 39/4631* (2023.05); *A61K 39/46447* (2023.05); *A61P 35/00* (2018.01); *C07K 16/3092* (2013.01); *A61K 2239/13* (2023.05); *A61K 2239/17* (2023.05); *A61K 2239/21* (2023.05); *A61K 2239/49* (2023.05); *A61K 2239/54* (2023.05); *A61K 2239/55* (2023.05)

(58) Field of Classification Search
CPC ................................................ A61K 39/46447
See application file for complete search history.

(56) References Cited

U.S. PATENT DOCUMENTS

| | | | |
|---|---|---|---|
| 7,709,226 B2 | 5/2010 | Foote | |
| 11,746,159 B2 * | 9/2023 | Bamdad | A61K 39/4611 |
| | | | 424/133.1 |
| 2016/0257758 A1 | 9/2016 | Gray et al. | |
| 2017/0204191 A1 | 7/2017 | Bamdad et al. | |
| 2017/0204196 A1 | 7/2017 | Bamdad et al. | |
| 2019/0290692 A1 | 9/2019 | Bamdad et al. | |
| 2022/0184120 A1 | 6/2022 | Bamdad et al. | |

FOREIGN PATENT DOCUMENTS

| | | |
|---|---|---|
| WO | WO-0157277 A2 | 8/2001 |
| WO | WO-2009103969 A8 | 1/2010 |
| WO | WO-2010042562 A2 | 4/2010 |
| WO | WO-2014028668 A2 | 2/2014 |
| WO | WO-2015116753 A1 | 8/2015 |
| WO | WO-2016130726 A1 | 8/2016 |
| WO | WO-2018071583 A2 | 4/2018 |
| WO | WO-2018132506 A1 | 7/2018 |
| WO | WO-2019124468 A1 | 6/2019 |
| WO | WO-2019133969 A2 | 7/2019 |
| WO | WO-2019165421 A1 | 8/2019 |
| WO | WO-2020080908 A1 | 4/2020 |
| WO | WO-2020117004 A1 | 6/2020 |
| WO | WO-2020146902 A2 | 7/2020 |
| WO | WO-2022027039 A1 | 2/2022 |

OTHER PUBLICATIONS

Shigeta et. al. Cancer Sci. 111(10):3639-3652. (2020) (Year: 2020).*
Abe et al., Structural analysis of the DF3 human breast carcinoma-associated protein. Cancer Res 49:2834-2839 (1989).
Al-Lazikani, B, et al., Standard Conformations For The Canonical Structures Of Immunoglobulins. Journal of Molecular Biology 273(4):927-948 (1997).
Arcangeli et al., Car T cell manufacturing from naive/stem memory T lymphocytes enhances antitumor responses while curtailing cytokine release syndrome. The Journal of Clinical Investigation 132(12):e150807 (2022).
Brentjens et al., Safety and persistence of adoptively transferred autologous CD19-targeted T cells in patients with relapsed or chemotherapy refractory Bcell leukemias. Blood 118(18):4817-4828 (2011).
Brudno et al., Chimeric antigen receptor T-cell therapies for lymphoma. Nature Reviews Clinical Oncology 15:31-46 (2017).
Carmon et al., Long Term Update on Phase I/II Trial with Immucin Anti-MUC1 Signal Peptide Vaccine for Multiple Myeloma Patients with Residual Disease or Progression. Blood 124(21):4768 (2014).
Chothia, C, et al., Structural Repertoire Of The Human VH Segments. Journal of Molecular Biology 227(3):799-817 (1992).
Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.
Co-pending U.S. Appl. No. 18/018,536, inventors Bamdad; Cynthia et al., filed on Jan. 27, 2023.
Co-pending U.S. Appl. No. 18/408,259, inventors Bamdad; Cynthia et al., filed on Jan. 9, 2024.
Courtenay-Luck, Chapter 8: Genetic Manipulation Of Monoclonal Antibodies. Monoclonal Antibodies: Production, Engineering and Clinical Application: 166-179 (1995).
Curigliano et al., Cancer-testis antigen expression in triple negative breast cancer. Annals of oncology: official journal of the European Society for Medical Oncology / ESMO 22(1):98-103 (2011).

(Continued)

*Primary Examiner* — Jessica H Roark
*Assistant Examiner* — Francesca Edgingtongiordan
(74) *Attorney, Agent, or Firm* — WILSON SONSINI GOODRICH & ROSATI

(57) ABSTRACT

Disclosed herein are chimeric antigen receptors (CARs) that target MUC1*. In some embodiments, the CARs have been optimized to reduce T cell exhaustion.

39 Claims, 10 Drawing Sheets

(4 of 10 Drawing Sheet(s) Filed in Color)

Specification includes a Sequence Listing.

(56) References Cited

OTHER PUBLICATIONS

Davila, et al., Chimeric antigen receptors for the adoptive T cell therapy of hematologic malignancies. International Journal of Hematology 99(4):361-371 (2014).
Denardo, David G, et al., Leukocyte Complexity Predicts Breast Cancer Survival And Functionally Regulates Response To Chemotherapy. Cancer Discovery 1(1):54-67 (2011).
Dudley et al. Adoptive Cell Transfer Therapy Following Non-Myeloablative but Lymphodepleting Chemotherapy for the Treatment of Patients With Refractory Metastatic Melanoma. J Clin Oncol. 23(10):2346-2357 (2005).
FDA Briefing Document: BLA 125646 Tisagenlecleucel https://www.fda.gov/downloads/AdvisoryCommittees/CommitteesMeetingMaterials/Drugs/OncologicDrugsAdvisoryCommittee/UCM566166.pdf Accessed Feb. 20, 2018.
Feucht et al. Calibration of CAR activation potential directs alternative T cell fates and therapeutic potency. Nat Med. 25(1):82-88 (2019).
Fiedler et al., A phase I study of PankoMab-GEX, a humanised glyco-optimised monoclonal antibody to a novel tumour-specific MUC1 glycopeptide epitope in patients with advanced carcinomas, European Journal of Cancer 63:55-63 (2016).
Finak et al., Stromal gene expression predicts clinical outcome in breast cancer. Nature Medicine 14(5):518-527 (2008).
Gendler et al., Cloning of partial cDNA encoding differentiation and tumor-associated mucin glycoproteins expressed by human mammary epithelium. Proc. Natl. Acad. Sci. U.S.A. 84:6060-6064 (1987).
Gendler, et al. Molecular cloning and expression of human tumor-associated polymorphic epithelial mucin. J Biol Chem. 265:15286-15293 (1990).
Hai et al., The relationship between MMP-2 and MMP-9 expression levels with breast cancer incidence and prognosis. Oncology Letters 14: 5865-5870 (2017).
Hikita et al. MUC1* Mediates the Growth of Human Pluripotent Stem Cells. PLoS One 3(10):1-13 [e3312] (2008).
Hilkens et al., Monoclonal antibodies against human milk-fat globule membranes detecting differentiation antigens of the mammary gland and its tumors. Int. J. Cancer 34:197-206 (1984).
Hudecek, et al. Adoptive T-cell therapy for B-cell malignancies. Expert review of hematology 2.5 (Oct. 2009): 517-532.
Huston, James S, et al., Protein Engineering Of Single-chain Fv Analogs And Fusion Proteins. Methods in Enzymology 203:46-96 (1991).
Hwu et al., The genetic modification of T cells for cancer therapy: an overview of laboratory and clinical trials.Cancer Detect Prev. 18(1):43-50 (1994).
June et al., Engineering lymphocyte subsets: tools, trials and tribulations. Nat Rev Immunol 9.10:704-716 (2009).
Kabat, Elvin A, et al., Attempts to Locate Complementarity-Determining Residues in the Variable Positions of Light and Heavy Chains. Annals of the New York Academy of Sciences 190:382-393 (1971).
Kabat, Elvin A, et al., Sequences Of Proteins Of Immunological Interest, NIH Publication No. 91-3242. U.S. Department of Health and Human Services, Public Health Service, National Institutes of Health 1:647-669 (1991).
Kalos, et al., T Cells with Chimeric Antigen Receptors Have Potent Antitumor Effects and Can Establish Memory in Patients with Advanced Leukemia. Science Translation Medicine 3:95ra73 (2011).
Kawalekar et al.: Distinct Signaling of Coreceptors Regulates Specific Metabolism Pathways and Impacts Memory Development in CAR T Cells. Immunity. 44:380-390 (2016).
Kershaw et al., Supernatural T cells: genetic modification of T cells for cancer therapy. Nature Reviews: Immunology 5(12):928-940 (2005).
Kim et al., Novel antibodies targeting MUC1-C showed anti-metastasis and growth-inhibitory effects on human breast cancer cells. Int J Mol Sci. 21(9):3258. doi: 10.3390/ijms21093258 (2020).
Kochenderfer et al., Abstract 765: Treatment of Chemotherapy-Refractory B-Cell Malignancies with Anti-CD19 Chimeric Antigen Receptor T Cells. Presented at the Annual Meeting of the American Society of Gene and Cell Therapy. New Orleans, LA. (2014).
Kochenderfer et al., Adoptive transfer of syngeneic T cells transduced with a chimeric antigen receptor that recognizes murine CD19 can eradicate lymphoma and normal B cells. Blood 116:3875-3886 (2010).
Kochenderfer et al., B-cell depletion and remissions of malignancy along with cytokine-associated toxicity in a clinical trial of anti-CD19 chimeric-antigen-receptor-transduced T cells. Blood 119(12):2709-2720 (2012).
Kochenderfer et al., Chemotherapy-refractory diffuse large B-cell lymphoma and indolent B-cell malignancies can be effectively treated with autologous T cells expressing an anti-CD19 chimeric antigen receptor, Journal of Clinical Oncology 33(6):540-549 (Feb. 20, 2015).
Kochenderfer et al., Chimeric antigen receptor-modified T cells in CLL. The New England Journal of Medicine 365(20):1937-1938 (2011).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Kufe, et al. Differential reactivity of a novel monoclonal antibody (DF3) with human malignant versus benign breast tumors. Hybridoma 3:223-232 (1984).
Lan et al., Cloning and sequencing of a human pancreatic tumor mucin cDNA. J Biol Chem. 265(25):15294-15299 (1990).
Larrick, James W, et al., PCR Amplification Of Antibody Genes. Methods 2(2):106-110 (1991).
Lefranc, Marie-Paule, et al., IMGT, the International ImMunoGeneTics Database. Nucleic Acids Research 27(1):209-212 (1999).
Lefranc, Marie-Paule, et al., The IMGT Unique Numbering for Immunoglobulins, T-Cell Receptors, and Ig-Like Domains. The Immunologist 7:132-136 (1999).
Lehmann. Identification of human triple-negative breast cancer subtypes and preclinical models for selection of targeted therapies. J Clinical Invest. 121(7):2750-2767 (2011).
Ligtnberg et al. Episialin, a carcinoma associated mucin, is generated by a polymorphic gene encoding splice variants with alternative amino termini. J. Biol. Chem. 265:5573-5578 (1990).
Maccallum, Robert M, et al., Antibody-Antigen Interactions: Contact Analysis And Binding Site Topography. Journal of Molecular Biology 262(5):732-745 (1996).
Mahanta et al. A Minimal Fragment of MUC1 Mediates Growth of Cancer Cells. PLoS One 3(4):e2054 (2008).
Maher et al. Human T-lymphocyte cytotoxicity and proliferation directed by a single chimeric TCRzeta /CD28 receptor. Nat Biotech 20(1):70-75 (2002).
Mahmoud et al., Tumor-infiltrating CD8+ lymphocytes predict clinical outcome in breast cancer. J Clin Oncol 29(15):1949-1955 (2011).
Majzner, Robbie G, et al., Tuning the Antigen Density requirement for CAR T Cell Activity. Cancer Discovery 10(5):702-723 (2020).
Martin, Andrew C, Chapter 3: Protein Sequence and Structure Analysis of Antibody Variable Domains. In Antibody Engineering, Kontermann and Diibel, Editions, Springer-Verlag, Berlin:422-439 (2001).
Maude, et al., Managing Cytokine Release Syndrome Associated With Novel T Cell-engaging Therapies. Cancer Journal 20(2):119-22 (2014).
Mcguckin et al., Prognostic significance of MUC1 epithelial mucin expression in breast cancer Human Pathology. 26(4):432-439 (1995).
Meyerholz, David K, et al., Principles And Approaches For Reproducible Scoring Of Tissue Stains In Research. Laboratory Investigation 98(7):844-855 (2019).
Morgan, R. A., et al., (2006), Cancer Regression in Patients After Transfer of Genetically Engineered Lymphocytes, Science 314:126-129.
Muller et al., High density oglycosylation on tandem repeat peptide from secretory MUC1 of T47D breast cancer cells. J. Biol. Chem. 274:18165-18172 (1999).

(56) References Cited

OTHER PUBLICATIONS

Kochenderfer et al., Eradication of B-lineage cells and regression of lymphoma in a patient treated with autologous T cells genetically engineered to recognize CD19 (Blood, 2010, 116:4099-4102) (Year: 2010).
Neelapu et al., Chimeric antigen receptor T-cell therapy—assessment and management of toxicities. Nat Rev Clin Oncol. 15(1):47-62 (2018).
Nemunaitis et al., Tolerability, humoral immune response, and disease control in phase 1 patients receiving ONT-10, a MUC1 liposomal vaccine. Journal of Clinical Oncology 32:3091 (2014).
Newrzela et al., Resistance of mature T cells to oncogene transformation. Blood 112(6):2278-2286 (2008).
Park et al., A Phase I Study of CD19-Targeted 19(T2)28z1xx CAR T Cells in Adult Patients with Relapsed or Refractory Diffuse Large B-Cell Lymphoma American Society of Hemtology, Abstract 163, Session 704. Cellular Immunotherapies: Early Phase and Investigational Therapies: Lymphoma Hematology Disease Topics & Pathways (2022).
Park, et al., Adoptive Transfer of Chimeric Antigen Receptor Re-directed Cytolytic T Lymphocyte Clones in Patients with Neuroblastoma. Mol Ther 15(4):825-833 (2007).
Patel et al., Cancer CARtography: charting out a new approach to cancer immunotherapy. Immunotherapy 6(6):675-678 (2014).
Pegram et al., Phase I dose escalation pharmacokinetic assessment of intravenous humanized anti-MUC1 antibody AS1402 in patients with advanced breast cancer. Breast Cancer Research 11(5):R73 (2009).
Porter et al., Chimeric antigen receptor-modified T cells in chronic lymphoid leukemia. N Engl J Med 365:725-733 (2011).
Quintarelli et al., Choice of costimulatory domains and of cytokines determines CAR T-cell activity in neuroblastoma. OncoImmunology 7(6):e1433518 (2018).
Quoix et al., TG4010 immunotherapy and first-line chemotherapy for advanced non-small-cell lung cancer (TIME): results from the phase 2b part of a randomised, double-blind, placebo-controlled, phase 2b/3 trial. Lancet Oncology 17(2):212-223 (2016).
Ram, Sripad, et al., Pixelwise H-score: A Novel Digital Image Analysis-based Metric To Quantify Membrane Biomarker Expression From Immunohistochemistry Images. PLOS One 16(9): 20 pages (2021).
Ren et al., Human MUC1 carcinoma-associated protein confers resistance to genotoxic anticancer agents. Cancer Cell 5(2):163-175 (2004).
Sadelain et al. Targeting tumours with genetically enhanced T lymphocytes. Nat Rev Cancer 3(1):35-45 (2003).
Schulert et al., Pathogenesis of macrophage activation syndrome and potential for cytokine-directed therapies. Annu Rev Med. 66:145-159 (2015).
Shah, Nirali N, et al., Mechanisms Of Resistance To CAR T Cell Therapy. Nature Reviews Clinical Oncology 16(6):372-385 (2019).
Smagghe et al. MUCI* ligand, NM23-H1, is a novel growth factor that maintains human stem cells in a more naive state. PLoS One 8(3):E58601 (2013).
Study of GO-203-2C Given Intravenously in Patients With Advanced Solid Tumors Including Lymphomas. https://ctv.veeva.com/study/study-of-go-203-2c-given-intravenously-in-patients-with-advanced-solid-tumors-including-lymphomas (2013).
Suhoski et al., Engineering artificial antigen-presenting cells to express a diverse array of co-stimulatory molecules. Molecular Therapy 15(5):981-988 (2007).
Takahashi et al., Feasibility study of personalized peptide vaccination for metastatic recurrent triple-negative breast cancer patients. Breast Cancer Research: BCR 16(4):R70 (2014).
Tchou et al., Mesothelin, a novel immunotherapy target for triple negative breast cancer. Breast cancer research and treatment. 133(2):799-804 (2012).
Thie et al., Rise and fall of an anti-MUC1 specific antibody. PLoS One 6(1):e15921 (2011).
Tramontano, A, et al., Framework Residue 71 Is a Major Determinant of the Position and Conformation of the Second Hypervariable Region in the VH Domains of Immunoglobulins. Journal of Molecular Biology 215(1):175-182 (1990).
Turtle et al. CD19 CAR-T cells of defined CD4+:CD8+ composition in adult B cell All patients. J Clin Invest 126(6):2123-2138 (2016).
Turtle et al., Immunotherapy of non-Hodgkin's lymphoma with a defined ratio of CD8+ and CD4+ CD19-specific chimeric antigen receptor-modified T cells. Sci Transl Med. 8(355):355ra116 (2016).
Turtle et al., Therapy of B Cell Malignancies with CD19-Specific Chimeric Antigen Receptor-Modified T Cells of Defined Subset Composition. Blood 124: Abstract 384 (2014).
Wang et al., Phase 1 studies of central memory-derived CD19 CAR T-cell therapy following autologous HSCT in patients with B-cell NHL. Blood 127:2980-2990 (2016).
Ward, et al., Genetic Manipulation and Expression of Antibodies. Monoclonal Antibodies: Principles and Applications, Wiley-Liss Inc:137-185 (1995).
Westgaard et al., Differentiation markers in pancreatic head adenocarcinomas: MUC1 and MUC4 expression indicates poor prognosis in pancreatobiliary differentiated tumours Histopathology 54(3):337-347 (2009).
Wreschner et al., Human epithelial tumor antigen cDNA sequences. Differential splicing may generate multiple splicing forms. Eur J Biochem 189:463-473 (1990).
Wrzesinski et al., Hematopoietic stem cells promote the expansion and function of adoptively transferred antitumor CD8 T cells. The Journal of Clinical Investigation 117(2):492-501 (2007).
Yousef et al. MMP-9 expression varies according to molecular subtypes of breast cancer. BMC Cancer 14:609 (2014).
Zaretsky et al., Expression of genes coding for pS2, c-erbB2, estrogen receptor and the H23 breast tumor-associated antigen. A comparative analysis in breast cancer. FEBS Lett. 265:46-50 (1990).
Baeuerle et al. Bispecific T-cell engaging antibodies for cancer therapy. Cancer Res 69:4941-4944 (2009).
Bamdad et al. Abstract 3330: MUC1* targeting CAR T. Cancer Research 77(13):3330 (2017).
Braga et al., Spatial and temporal expression of an epithelial mucin, Muc-1, during mouse development. Development 115(2):427-437 (1992).
Brinkmann et al. The making of bispecific antibodies. MABS 9(2):182-212 (2017).
Carter et al. A Primitive Growth Factor, NME7AB , Is Sufficient to Induce Stable Naïve State Human Pluripotency; Reprogramming in This Novel Growth Factor Confers Superior Differentiation. Stem Cells 34(4):847-59 (2016).
Chen et al. Multiple Cancer/Testis Antigens Are Preferentially Expressed in Hormone-Receptor Negative and High-Grade Breast Cancers. PLoS One 6(3):e17876 (2011).
Chothia, Cyrus and Lesk, Arthur M. Canonical Structures for the Hypervariable Regions of Immunoglobulins. Journal of Molecular Biology 196(4):901-917 (1987).
Cohen, David A. et al. Interobserver agreement among pathologists for semiquantitative hormone receptor scoring in breast carcinoma. Am J Clin Pathol 138(6):796-802 (2012).
Czajkowsky et al. Fc-fusion proteins: new developments and future perspectives. EMBO Mol Med. 4(10):1015-1028 (2012).
Dai et al. Chimeric Antigen Receptors Modified T-Cells for Cancer Therapy. J Natl Cancer Inst. 108(7):djv439 (2016).
Denkert et al., Tumor-associated lymphocytes as an independent predictor of response to neoadjuvant chemotherapy in breast cancer. Journal of clinical oncology: official journal of the American Society of Clinical Oncology 28(1):105-113 (2010).
Falahat, Rana et al. A Cell ELISA for the quantification of MUC1 mucin (CD227) expressed by cancer cells of epithelial and neuroectodermal origin. Cell Immunol 298(1-2):96-103 (2015).
Fessler et al. MUC1* is a determinant of trastuzumab (Herceptin) resistance in breast cancer cells. Breast Cancer Res Treat 118:113-134 (2009).
Hanisch et al., MUC1: the polymorphic appearance of a human mucin. Glycobiology 10:439-449 (2000).

(56) References Cited

OTHER PUBLICATIONS

Hombach et al. 0X40 costimulation by a chimericantigen receptor abrogates CD28 and IL-2 induced IL-10 secretion by redirectedCD4(+) T cells. Oncoimmunology 1(4):458-466 (2012).

Lamers et al., Treatment of metastatic renal cell carcinoma with CAIX CAR-engineered T cells: clinical evaluation and management of on-target toxicity. Molecular Therapy : the Journal of the American Society of Gene Therapy 21(4):904-912 (2013).

Lee et al., Current concepts in the diagnosis and management of cytokine release syndrome. Blood, 124:188-195 (2014).

Long et al. 4-1BB Costimulation Ameliorates T Cell Exhaustion Induced by Tonic Signaling of Chimeric Antigen Receptors. Nat Med 21(6):581-590 (2015).

Loskog et al. Addition of the CD28 signaling domain to chimeric T-cell receptors enhances chimeric T-cell resistance to T regulatory cells. Leukemia 20(10):1819-1828 (2006).

Lyakh et al. Expression of NFAT-Family proteins in normal human T cells, Molecular And Cellular Biology 17(5):2475-2484 (1997).

Lynn et al. c-Jun overexpression in CAR T cells induces exhaustion resistance. Nature 576(7786):293-300 (2019).

Macian. NFAT Proteins: Key Regulators of T-Cell Development and Function. Nat. Rev. Immunol. 5(6):472-84 (2005).

Milone et al. Chimeric receptors containing CD137 signal transduction domains mediate enhanced survival of T cells and increased antileukemic efficacy in vivo. Mol Ther 17(8):1453-1464 (2009).

Owyong et al. MMP9 modulates the metastatic cascade and immune landscape for breast cancer anti-metastatic therapy. Life Sci Alliance 2(6):e201800226 (2019).

PCT/US2020/013410 International Search Report and Written Opinion dated Jul. 23, 2020.

PCT/US2020/013410 Invitation to Pay Additional Fees dated May 1, 2020.

PCT/US2021/071017 International Search Report and Written Opinion dated Dec. 29, 2021.

Pule et al. A chimeric T cell antigen receptor that augments cytokine release and supports clonal expansion of primary human T cells. Mol Ther 12(5):933-941 (2005).

Rao et al. Transcription factors of the NFAT family: regulation and function. Annu Rev Immunol. 15:707-747 (1997).

Rudikoff, et al. Single Amino Acid Substitution Altering Antigen-binding Specificity. PNAS USA 79(6):1979-1983 (1982).

Salter, et al., Phosphoproteomic Analysis of Chimeric Antigen Receptor Signaling Reveals Kinetic and Quantitative Differences That Affect Cell Function. Science Signaling 11(544): 18 Pages (2018).

Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).

Spiess, Christoph et al. Alternative Molecular Formats and Therapeutic Applications for Bispecific Antibodies. Molecular Immunology 67(2 Pt A):95-106 (2015).

Tiller et al. Facile Affinity Maturation of Antibody Variable Domains Using Natural Diversity Mutagenesis. Front. Immunol. 8:986 (2017).

U.S. Appl. No. 15/549,942 Office Action dated Jan. 11, 2023.
U.S. Appl. No. 16/539,247 Office Action dated Jun. 1, 2022.
U.S. Appl. No. 17/817,515 Office Action dated Apr. 26, 2023.
U.S. Appl. No. 18/408,259 Office Action dated Jul. 1, 2024.

Van't Veer et al. Gene expression profiling predicts clinical outcome of breast cancer. Nature 415(6871):530-536 (2002).

* cited by examiner

CHIMERIC ANTIGEN RECEPTOR COMPOSITIONS AND METHODS FOR TREATING MUC1* DISEASES

CROSS REFERENCE

This application claims the benefit of the U.S. Provisional Application No. 63/482,972, filed Feb. 2, 2023, which is incorporated herein by reference in its entirety.

SEQUENCE LISTING

The instant application contains a Sequence Listing which has been submitted electronically in XML file format and is hereby incorporated by reference in its entirety. Said XML copy, created on Jan. 4, 2024, is named 56699-757_202_SL.xml and is 48,362 bytes in size.

SUMMARY

Disclosed herein is a chimeric antigen receptor (CAR) comprising a MUC1*binding single chain antibody domain comprising heavy chain (HC) complementarity determining regions (CDRs) comprising a HC-CDR1 comprising SEQ ID NO: 18, a HC-CDR2 comprising SEQ ID NO: 19, and a HC-CDR3 comprising SEQ ID NO: 20; and light chain (LC) CDRs comprising a LC-CDR1 comprising SEQ ID NO: 21, a LC-CDR2 comprising SEQ ID NO: 22, and a LC-CDR3 comprising SEQ ID NO: 23; a hinge region comprising SEQ ID NO: 40; a transmembrane domain comprising SEQ ID NO: 41; and a signaling domain comprising SEQ ID NO: 44. In some embodiments, the CAR further comprises a costimulatory domain comprising SEQ ID NO: 42. In some embodiments, the MUC1* binding single chain antibody domain comprises a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2. In some embodiments, the linker comprises an amino acid sequence of the formula (GGGGS) n, wherein n is a number from 1 to 5 (SEQ ID NO: 50). In some embodiments, the linker comprises SEQ ID NO: 24. In some embodiments, the linker comprises any one of SEQ ID NOs: 26, 28, 30, 32, 34, 36, or 38. In some embodiments, the MUC1* binding single chain antibody domain comprises SEQ ID NO: 39. In some embodiments, the hinge region and the transmembrane domain together comprise SEQ ID NO: 3. In some embodiments, a cytoplasmic domain comprising the costimulatory domain and the signaling domain comprises SEQ ID NO: 4. In some embodiments, the CAR comprises a sequence having at least 95% identity to SEQ ID NO: 48. In some embodiments, the CAR consists of SEQ ID NO: 48. In some embodiments, Disclosed herein is an immune cell comprising any of the CARs above. Disclosed herein is a nucleic acid encoding any of the CARs above. Disclosed herein is a vector comprising a nucleic acid encoding any of the CARs above and an immune cell comprising the vector.

Disclosed herein is a method of treating a MUC1* positive cancer in an individual, comprising administering to the individual an engineered immune cell expressing a CAR comprising a MUC1* binding single chain antibody domain comprising heavy chain (HC) complementarity determining regions (CDRs) comprising a HC-CDR1 comprising SEQ ID NO: 18, a HC-CDR2 comprising SEQ ID NO: 19, and a HC-CDR3 comprising SEQ ID NO: 20; and light chain (LC) CDRs comprising a LC-CDR1 comprising SEQ ID NO: 21, a LC-CDR2 comprising SEQ ID NO: 22, and a LC-CDR3 comprising SEQ ID NO: 23; a hinge region comprising SEQ ID NO: 40; a transmembrane domain comprising SEQ ID NO: 41; and a signaling domain comprising SEQ ID NO: 44. In some embodiments, the CAR further comprises a costimulatory domain comprising SEQ ID NO: 42. In some embodiments, the MUC1* binding single chain antibody domain comprises a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2. In some embodiments, the linker comprises an amino acid sequence of the formula (GGGGS) n, wherein n is a number from 1 to 5 (SEQ ID NO: 50). In some embodiments, the linker comprises SEQ ID NO: 24. In some embodiments, the linker comprises any one of SEQ ID NOs: 26, 28, 30, 32, 34, 36, or 38. In some embodiments, the MUC1* binding single chain antibody domain comprises SEQ ID NO: 39. In some embodiments, the hinge region and the transmembrane domain together comprise SEQ ID NO: 3. In some embodiments, a cytoplasmic domain comprising the costimulatory domain and the signaling domain comprises SEQ ID NO: 4. In some embodiments, the CAR comprises a sequence having at least 95% identity to SEQ ID NO: 48. In some embodiments, the CAR consists of SEQ ID NO: 48. In some embodiments, the MUC1* positive cancer comprises a solid tumor. In some embodiments, the MUC1* positive cancer is breast cancer. In some embodiments, the MUC1* positive cancer is lung cancer. In some embodiments, the MUC1* positive cancer is pancreatic cancer. In some embodiments, a section of a tumor of the MUC1* positive cancer has low MUC1* expression characterized by an anti-MUC1* H-score of 100 or less. In some embodiments, a cell of the MUC1* positive cancer reacts with a MUC1* antibody in an immunohistochemistry assay. In some embodiments, a cell of the MUC1* positive cancer reacts with a MUC1* antibody in an enzyme linked immunosorbent assay (ELISA). In some embodiments, a cell of the MUC1* positive cancer reacts with a MUC1* antibody in flow cytometry assay. In some embodiments, the method reduces tumor recurrence compared to treatment with an immune cell comprising an otherwise identical CAR wherein the signaling domain comprises SEQ ID NO: 43 instead of SEQ ID NO: 44. In some embodiments, the engineered immune cell is a T cell. In some embodiments, the engineered immune cell is an NK cell. In some embodiments, the T cell remains active after 6 or more days of stimulation with MUC1* or a synthetic MUC1* peptide comprising SEQ ID NO: 49. In some embodiments, the T cell is derived from a healthy donor. In some embodiments, the T cell is derived from an individual with a MUC1* positive cancer.

Disclosed herein are methods of killing a MUC1* positive cancer cell comprising contacting the cell with an engineered T cell expressing a chimeric antigen receptor comprising: a MUC1* binding single chain antibody (scFv) domain comprising heavy chain (HC) complementarity determining regions (CDRs) comprising SEQ ID NOs: 18-20 and light chain (LC) CDRs comprising SEQ ID NOs: 21-23, a hinge region comprising SEQ ID NO: 40, a transmembrane domain comprising SEQ ID NO: 41, a costimulatory domain comprising SEQ ID NO: 42, and a signaling domain comprising SEQ ID NO: 44. In some embodiments, the MUC1* positive cancer cell is a breast cancer cell. In some embodiments, the MUC1* positive cancer cell is a lung cancer cell. In some embodiments, the MUC1* positive cancer cell is a pancreatic cancer cell. In some embodiments, the MUC1* positive cancer cell has low MUC1* expression. Low MUC1* expression may be indicated by an anti-MUC1* H-score of 120 or less, 100 or less, 80 or less, 60 or less, 40 or less, 30 or less, 20 or less, or 10 or less. In some embodiments, a section of a tumor comprising the MUC1* positive cancer cell has low MUC1* expression characterized by an anti-MUC1* H-score of 120 or less, 100 or less, 80 or less, 60 or less, 40 or less, 30 or less, 20 or less, or 10 or less. In some embodiments, a tumor comprising the MUC1* positive cancer cell re-acts with a MUC1* antibody in an immunohistochemistry assay, an enzyme linked immunosorbent assay (ELISA), or a flow cytometry assay. In some embodiments, the T cell remains active after 6 days of stimulation with MUC1*. the T cell is derived from a healthy donor. In some embodiments, the T cell is derived from an individual with a MUC1* positive cancer. In some embodiments, the MUC1* binding domain comprises a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2. In some embodiments, the linker comprises an amino acid sequence of the formula (GGGGS)n wherein n is a number from 1 to 5 (SEQ ID NO: 50). In some embodiments, the linker comprises SEQ ID NO: 24. In some embodiments, the linker comprises any one of SEQ ID NOs:26, 28, 30, 32, 34, 36, or 38. the MUC1* binding domain comprises SEQ ID NO: 39. In some embodiments, the hinge and transmembrane domain together comprise SEQ ID NO: 3. In some embodiments, a cytoplasmic domain comprising the costimulatory domain and the signaling domain comprises SEQ ID NO: 4. In some embodiments, the chimeric antigen receptor comprises a sequence having at least 95% identity to SEQ ID NO: 48. In some embodiments, the chimeric antigen receptor consists of SEQ ID NO: 48.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figures 1A, 1B, 1C:
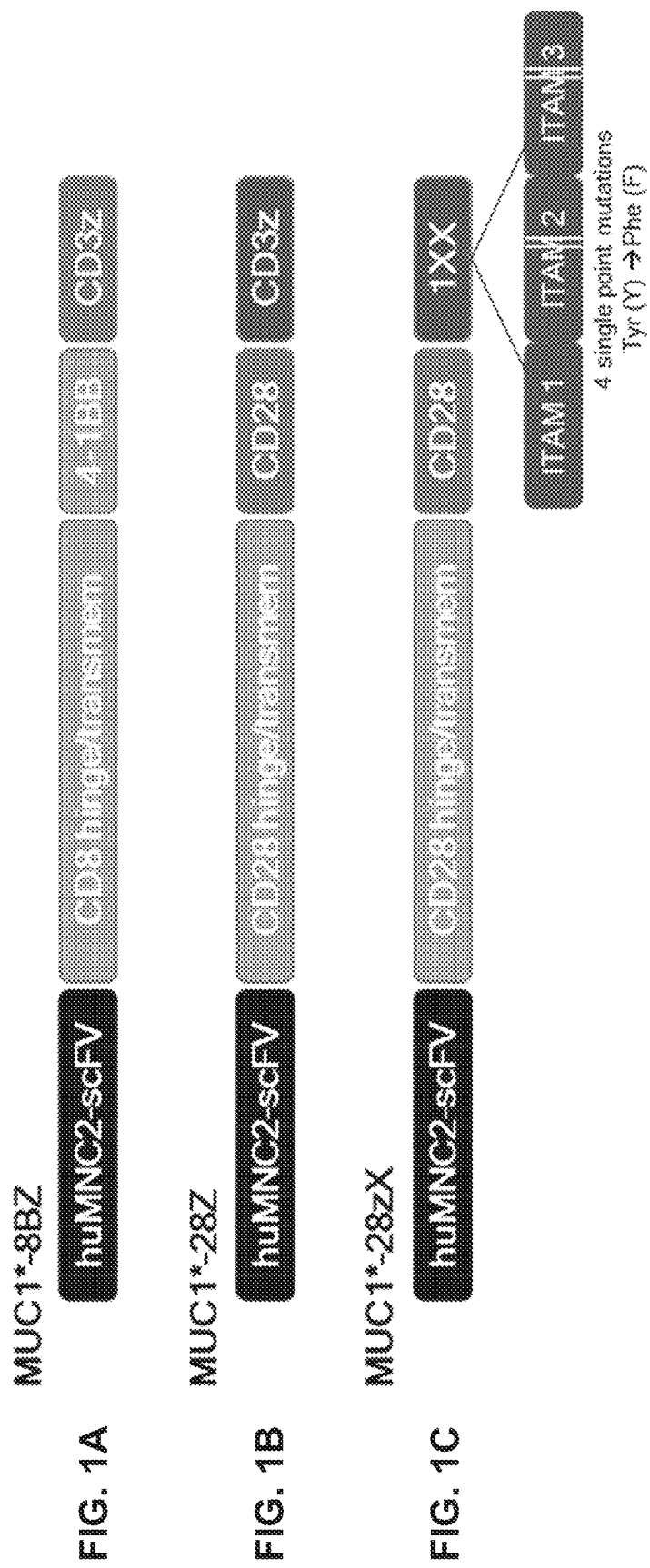
FIGS. 1A-1C illustrate the structure of anti-MUC1* chimeric antigen receptors (CARs) MUC1*-8BZ (FIG. 1A), MUC1*-28Z-3z (FIG. 1B) and MUC1*-28zX (FIG. 1C).

Chimeric antigen receptors (CARs) are molecules that include a targeting domain specific for a cell surface antigen, a transmembrane domain, and a T cell signaling moiety. When expressed on the surface of an immune cell, such as a T cell, the CARs mediate binding to a target cell and activate the T cells, ultimately inducing the target cell lysis. CARs are a promising approach to treat hematological malignancies, including non-Hodgkin lymphoma, B-cell acute lymphoblastic leukemia, and multiple myeloma. However, T cell exhaustion remains a challenge in CAR-T therapies and there remains a need for effective immunotherapies to treat solid tumors as well as hematological malignancies.

MUC1*

MUC1* is an ideal target for cancer drugs as it is aberrantly expressed on over 75% of all solid tumor cancers and is likely overexpressed on an even higher percentage of metastatic cancers.

MUC1* is a variant form of the mucin MUC1 that is found on over 75% of solid tumors. On normal tissues, MUC1 is expressed on the apical surface of polarized cells as a Type I membrane protein with an extracellular N-terminus having hundreds of highly o-glycosylated tandem repeats followed by a self-aggregation domain, a transmembrane domain, and a cytoplasmic tail. MUC1* is a MIUC1 cleavage product with a truncated extracellular domain that functions as a growth factor receptor. Metalloproteinase cleavage of MUC1 clips off the tandem repeat and self-aggregation domains, leaving behind a newly accessible ligand-binding domain of about 45 amino acids. MUC1* activation by growth factor ligands that dimerize MUC1* such as NME7 promotes the growth and metastasis of cancer cells by inducing MAP kinase phosphorylation and other intracellular growth signals. Proteolytic elimination of the self-aggregation domain permits MUC1* to redistribute over the entire cell surface.

Full-length MUC1 runs on SDS-polyacrylamide gels with a molecular weight of about 150-350 kDa, depending on the number of tandem repeats and glycans, and can be detected with the commercially available VU4H5 and HMPV antibodies. MUC1* has a calculated molecular weight of 16-18 kDa, depending on cleavage site, and runs at about 25 kDa on SDS-polyacrylamide gels. The C2 antibody binds to a conformational epitope of MUC1* that is not accessible on the full-length MUC1 protein found on normal tissues.

After MUC1 is cleaved to MUC1*, release of the bulk of the extracellular domain of MUC1 unmasks a binding site for ligands such as NME1, NME6, NME7, NME7AB, NME7-X1 or NME8. Ligands that dimerize MIUC1* activate downstream signaling by MIUC1*, which can induce growth and/or metastasis in cancer cells.

Chimeric Antigen Receptor Compositions

Disclosed herein are CAR compositions that target MUC1*. In some embodiments, the CAR constructs that target MUC1*, have been optimized to reduce T cell exhaustion relative to a control CAR composition that targets MUC1*. In some embodiments, the control CAR comprises the amino acid sequence according to SEQ ID NO: 47. In some embodiments, the CAR comprises a mutated CD3 zeta signaling domain sequence. In some embodiments, the mutated CD3 zeta signaling domain contains a point mutation of a tyrosine to a phenylalanine in at least one ITAM motif, at least two ITAM motifs, or at least three ITAM motifs. In some embodiments, the mutated CD3 zeta signaling domain contains a point mutation of tyrosine to a phenylalanine in the second, and third ITAM motif, whereas the first ITAM motif is not mutated.

Disclosed herein are chimeric antigen receptors (CARs) that comprise an amino acid sequence that comprises in an N-terminal to C-terminal order: (a) a first region comprising a signal sequence; (b) a second region comprising: i) a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2, or (ii) a light chain variable domain that comprises an amino acid sequence that has at least 90% identity to SEQ ID NO: 2, a linker, and a heavy chain variable domain that comprises an amino acid sequence that has at least 90% identity to SEQ ID NO: 1; (c) a third region comprising a hinge sequence and a transmembrane domain sequence that comprises an amino acid sequence that has at least 85% identity to SEQ ID NO: 3; and (d) a fourth region comprising a costimulatory domain sequence and a signaling domain sequence wherein the fourth region comprises an amino acid sequence that has at least 90% identity to SEQ ID NO: 4. In some embodiments the signal sequence is cleaved off from the CAR during its biosynthesis to yield a mature CAR polypeptide.

TABLE 1

Chimeric Antigen Receptor Sequences

| Region of CAR | Description | Sequence | SEQ ID NO: |
|---|---|---|---|
| Second Region | C2 heavy chain variable domain | EVQLVESGGGLVKPGGSLRL SCAASGFTFSGYAMSWVRQA PGKGLEWVSTISSGGTYIYY PDSVKGRFTISRDNAKNSLY LQMNSLRAEDTAVYYCARLG GDNYYEYFDVWGKGTTVTVS S | 1 |
| Second Region | C2 light chain variable domain | DIVLTQSPASLAVSPGQRAT ITCRASKSVSTSGYSYMHWY QQKPGQPPKLLIYLASNLES GVPARFSGSGSGTDFTLTIN PVEANDTANYYCQHSRELPF TFGGGTKVEIKRT | 2 |
| Third Region | Hinge and Transmembrane | KHLCPSPLFPGPSKPFWVLV VVGGVLACYSLLVTVAFIIF WV | 3 |
| Fourth Region | Costimulatory domain sequence and signaling domain sequence | RSKRSRLLHSDYMNMTPRRP GPTRKHYQPYAPPRDFAAYR SRVKFSRSADAPAYKQGQNQ LYNELNLGRREEYDVLDKRR GRDPEMGGKPRRKNPQEGLF NELQKDKMAEAFSEIGMKGE RRRGKGHDGLFQGLSTATKD TFDALHMQALPPR | 4 |

First Region

In some embodiments, the signal sequence comprises an amino acid sequence that has at least 90% identity to any one of SEQ ID NOs: 5, 7, 9, 11, 13, 15, or 17. In some embodiments, the signal sequence comprises an amino acid sequence that has at least 95% identity to any one of SEQ ID NOs: 5, 7, 9, 11, 13, 15, or 17. In some embodiments, the signal sequence comprises the amino acid sequence according to any one of SEQ ID NOs: 5, 7, 9, 11, 13, 15, or 17.

In some embodiments, the signal sequence comprises an amino acid sequence that has at least 90% identity to SEQ ID NO: 5. In some embodiments, the signal sequence comprises an amino acid sequence that has at least 95% identity to SEQ ID NO: 5. In some embodiments, the signal sequence comprises the amino acid sequence according to SEQ ID NO: 5.

In some embodiments, the signal sequence comprises an amino acid sequence that has at least 90% identity to SEQ ID NO: 7. In some embodiments, the signal sequence comprises an amino acid sequence that has at least 95% identity to SEQ ID NO: 7. In some embodiments, the signal sequence comprises the amino acid sequence according to SEQ ID NO: 7.

In some embodiments, the signal sequence comprises an amino acid sequence that has at least 90% identity to SEQ ID NO: 9. In some embodiments, the signal sequence comprises an amino acid sequence that has at least 95% identity to SEQ ID NO: 9. In some embodiments, the signal sequence comprises the amino acid sequence according to SEQ ID NO: 9.

In some embodiments, the signal sequence comprises an amino acid sequence that has at least 90% identity to SEQ ID NO: 11. In some embodiments, the signal sequence comprises an amino acid sequence that has at least 95% identity to SEQ ID NO: 11. In some embodiments, the signal sequence comprises the amino acid sequence according to SEQ ID NO: 11.

In some embodiments, the signal sequence comprises an amino acid sequence that has at least 90% identity to SEQ ID NO: 13. In some embodiments, the signal sequence comprises an amino acid sequence that has at least 95% identity to SEQ ID NO: 13. In some embodiments, the signal sequence comprises the amino acid sequence according to SEQ ID NO: 13.

In some embodiments, the signal sequence comprises an amino acid sequence that has at least 90% identity to SEQ ID NO: 15. In some embodiments, the signal sequence comprises an amino acid sequence that has at least 95% identity to SEQ ID NO: 15. In some embodiments, the signal sequence comprises the amino acid sequence according to SEQ ID NO: 15.

In some embodiments, the signal sequence comprises an amino acid sequence that has at least 90% identity to SEQ ID NO: 17. In some embodiments, the signal sequence comprises an amino acid sequence that has at least 95% identity to SEQ ID NO: 17. In some embodiments, the signal sequence comprises the amino acid sequence according to SEQ ID NO: 17.

TABLE 2

Signal Sequences

| Region of CAR | Description | Sequence | SEQ ID NO: |
|---|---|---|---|
| First | CD8 | MALPVTALLLPLALLLHAARP | 5 |
| First | Human IL2 DNA | atgtacaggatgcagctgct gagctgcatcgccctgagcc tggccctggtgaccaacagc | 6 |
| First | Human IL2 aa | MYRMQLLSCIALSLALVINS | 7 |
| First | Granulocyte-macrophage colony-stimulating factor (GM-CSF) a chain DNA | atgtggctgcagagcctgct gctgctgggcaccgtggcct gcagcatcagc | 8 |
| First | Granulocyte-macrophage colony-stimulating factor (GM-CSF) a chain aa | MWLQSLLLLGTVACSIS | 9 |
| First | murine Ig-kappa (IgK) DNA | atggagacagacacactcct gctatgggtactgctgctct gggttccaggttccactggt | 10 |
| First | murine Ig-kappa (IgK) aa | METDTLLLWVLLLWVPGSTG | 11 |
| First | Human Ig-kappa (IgK) DNA | atggacatgagggtgcccgc ccagctgctgggcctgctgc tgctgtggctgaggggcgcc aggtgc | 12 |
| First | Human Ig-kappa (IgK) aa | MDMRVPAQLLGLLLLWLRGA RC | 13 |
| First | CD33 DNA | atgcccctgctgctgctgct gcccctgctgtgggccggcg ccctggcc | 14 |
| First | CD33 aa | MPLLLLLPLLWAGALA | 15 |
| First | tPA Human tissue plasminogen activator DNA | atggacgccatgaagagggg cctgtgctgcgtgctgctgc tgtgcggcgccgtgttcgtg agccccagc | 16 |
| First | tPA Human tissue plasminogen activator aa | MDAMKRGLCCVLLLCGAVFV SPS | 17 |

Second Region

In some embodiments, the second region comprises in an N-terminal to C-terminal order the heavy chain variable domain that comprises an amino acid sequence that has at least 90% identity to SEQ ID NO: 1, the linker, and the light chain variable domain that comprises an amino acid sequence that has at least 9000 identity to SEQ TD NO: 2.

In some embodiments, the second region comprises in an N-terminal to C-terminal order the light chain variable domain that comprises an amino acid sequence that has at least 90% identity to SEQ ID NO: 2, the linker, and the heavy chain variable domain that comprises an amino acid sequence that has at least 90% identity to SEQ TD NO: 1.

In some embodiments, the heavy chain variable domain comprises complementarity determining regions (CDRs) HC-CDR1, HC-CDR2, and HC-CDR3, wherein the HC-CDR1, the HC-CDR2, and the HC-CDR3 comprise the amino acid sequences: HC-CDR1: SEQ ID NO: 18; HC-CDR2: SEQ ID NO: 19; HC-CDR3: SEQ ID NO: 20.

In some embodiments, the light chain variable domain comprises complementarity determining regions (CDRs) LC-CDR1, LC-CDR2, and LC-CDR3, wherein the LC-CDR1, the LC-CDR2, and the LC-CDR3 comprise the amino acid sequences: LC-CDR1: SEQ ID NO: 21; LC-CDR2: SEQ ID NO: 22; LC-CDR3: SEQ ID NO: 23.

In some embodiments, the heavy chain variable domain comprises complementarity determining regions (CDRs)

HC-CDR1, HC-CDR2, and HC-CDR3, wherein the HC-CDR1, the HC-CDR2, and the HC-CDR3 comprise the amino acid sequences: HC-CDR1: SEQ ID NO: 18; HC-CDR2: SEQ ID NO: 19; HC-CDR3: SEQ ID NO: 20 and the light chain variable domain comprises complementarity determining regions (CDRs) LC-CDR1, LC-CDR2, and LC-CDR3, wherein the LC-CDR1, the LC-CDR2, and the LC-CDR3 comprise the amino acid sequences: LC-CDR1: SEQ ID NO: 21; LC-CDR2: SEQ ID NO: 22; LC-CDR3: SEQ ID NO: 23.

In some embodiments, the heavy chain variable domain comprises an amino acid sequence that has at least 95% identity to SEQ ID NO: 1. In some embodiments, the heavy chain variable domain comprises an amino acid sequence that has at least 98% identity to SEQ ID NO: 1. In some embodiments, the heavy chain variable domain comprises an amino acid sequence that has at least 99% identity to SEQ ID NO: 1. In some embodiments, the heavy chain variable domain comprises the amino acid sequence according to SEQ ID NO: 1.

In some embodiments, the light chain variable domain comprises an amino acid sequence that has at least 95% identity to SEQ ID NO: 2. In some embodiments, the light chain variable domain comprises an amino acid sequence that has at least 98% identity to SEQ ID NO: 2. In some embodiments, the light chain variable domain comprises an amino acid sequence that has at least 99% identity to SEQ ID NO: 2. In some embodiments, the light chain variable domain comprises the amino acid sequence according to SEQ ID NO: 2.

In some embodiments, the linker comprises an amino acid sequence that has at least 90% identity to any one of SEQ ID NOs: 24, 26, 28, 30, 32, 34, 36, or 38. In some embodiments, the linker comprises an amino acid sequence that has at least 95% identity to any one of SEQ ID NOs: 24, 26, 28, 30, 32, 34, 36, or 38. In some embodiments, the linker comprises the amino acid sequence according to any one of SEQ ID NOs: 24, 26, 28, 30, 32, 34, 36, or 38.

In some embodiments, the linker comprises an amino acid sequence of the formula (GGGGS)n wherein n is a number from 1 to 5 (SEQ ID NO: 50).

In some embodiments, the linker comprises an amino acid sequence that has at least 90% identity to SEQ ID NO: 24. In some embodiments, the linker comprises an amino acid sequence that has at least 98% identity to SEQ ID NO: 24. In some embodiments, the linker comprises the amino acid sequence according to SEQ ID NO: 24.

In some embodiments, the linker comprises an amino acid sequence that has at least 90% identity to SEQ ID NO: 26. In some embodiments, the linker comprises an amino acid sequence that has at least 98% identity to SEQ ID NO: 26. In some embodiments, the linker comprises the amino acid sequence according to SEQ ID NO: 26.

In some embodiments, the linker comprises an amino acid sequence that has at least 90% identity to SEQ ID NO: 28. In some embodiments, the linker comprises an amino acid sequence that has at least 98% identity to SEQ ID NO: 28. In some embodiments, the linker comprises the amino acid sequence according to SEQ ID NO: 28.

In some embodiments, the linker comprises an amino acid sequence that has at least 90% identity to SEQ ID NO: 30. In some embodiments, the linker comprises an amino acid sequence that has at least 98% identity to SEQ ID NO: 30. In some embodiments, the linker comprises the amino acid sequence according to SEQ ID NO: 30.

In some embodiments, the linker comprises an amino acid sequence that has at least 90% identity to SEQ ID NO: 32. In some embodiments, the linker comprises an amino acid sequence that has at least 98% identity to SEQ ID NO: 32. In some embodiments, the linker comprises the amino acid sequence according to SEQ ID NO: 32.

In some embodiments, the linker comprises an amino acid sequence that has at least 90% identity to SEQ ID NO: 34. In some embodiments, the linker comprises an amino acid sequence that has at least 98% identity to SEQ ID NO: 34. In some embodiments, the linker comprises the amino acid sequence according to SEQ ID NO: 34.

In some embodiments, the linker comprises an amino acid sequence that has at least 90% identity to SEQ ID NO: 36. In some embodiments, the linker comprises an amino acid sequence that has at least 98% identity to SEQ ID NO: 36. In some embodiments, the linker comprises the amino acid sequence according to SEQ ID NO: 36.

In some embodiments, the linker comprises an amino acid sequence that has at least 90% identity to SEQ ID NO: 38. In some embodiments, the linker comprises an amino acid sequence that has at least 98% identity to SEQ ID NO: 38. In some embodiments, the linker comprises the amino acid sequence according to SEQ ID NO: 38.

In some embodiments, the linker comprises an amino acid sequence that has at least 90% identity to SEQ ID NO: 24. In some embodiments, the linker comprises an amino acid sequence that has at least 9800 identity to SEQ TD NO: 24. In some embodiments, the linker comprises the amino acid sequence according to SEQ ID NO: 24. In some embodiments, the second region comprises an amino acid sequence that has at least 9500 identity to SEQ ID NO: 39. In some embodiments, the second region comprises an amino acid sequence that has at least 98% identity to SEQ TD NO: 39. In some embodiments, the second region comprises an amino acid sequence that has at least 9900 identity to SEQ ID NO: 39. In some embodiments, the second region comprises the amino acid sequence according to SEQ TD NO: 39.

TABLE 3

Second Region Sequences*

| Region of CAR | Description | Sequence | SEQ ID NO: |
|---|---|---|---|
| Second | HC-CDR1 | GYAMS | 18 |
| Second | HC-CDR2 | TISSGGTYIYYPDSVKGR | 19 |
| Second | HC-CDR3 | LGGDNYYEYFDV | 20 |
| Second | LC-CDR1 | RASKSVSTSGYSYMH | 21 |
| Second | LC-CDR2 | LASNLES | 22 |
| Second | LC-CDR3 | QHSRELPFT | 23 |
| Second | Linker | GGGGSGGGGSGGGGS | 24 |
| Second | Linker 20 DNA | ggtggcggtggttcaggtgg tgggggctctggcgggggtg gcagcggcggaggagggtca | 25 |
| Second | Linker 20 aa | GGGGSGGGGSGGGGSGGGGS | 26 |
| Second | Linker 25 DNA | ggtggcggtggttcaggtgg tgggggctctggcgggggtg gcagcggcggaggagggtca ggaggaggaggtagt | 27 |

TABLE 3-continued

Second Region Sequences*

| Region of CAR | Description | Sequence | SEQ ID NO: |
|---|---|---|---|
| Second | Linker 25 aa | GGGGSGGGGSGGGGSGGGGS GGGGS | 28 |
| Second | Linker 218S DNA | ggatctacaagcggaagcgg caagcctggctccggcgagg gcagcaccaagggc | 29 |
| Second | Linker 218S aa | GSTSGSGKPGSGEGSTKG | 30 |
| Second | Linker 32 DNA | ggggggttccggtggggatc tggaggtggcagcggtggtg gggggatcaggtggtgggg gtcaggcggaggcggttcag gcggcggtgggtca | 31 |
| Second | Linker 32 aa | GGSGGGSGGGSGGGGSGGG GSGGGGSGGGGS | 32 |
| Second | Linker R18 DNA | ggcggcagcagcaggagcag cagcagcggcggcggcggca gcggcggggcggc | 33 |
| Second | Linker R18 aa | GGSSRSSSSGGGGSGGGG | 34 |
| Second | Linker GS18 DNA | ggcagcaccagcggcggcgg cagcggcggcggcagcggcg gcggcggcagcagc | 35 |
| Second | Linker GS18 aa | GSTSGGGSGGGSGGGGSS | 36 |
| Second | Linker 14 DNA | ggcggcagcggcggcagcgg cggcagcggcggcagcggcg gc | 37 |
| Second | Linker 14 aa | GGSGGSGGSGGSGQ | 38 |
| Second | C2 scFv | EVQLVESGGGLVKPGGSLRL SCAASGFTFSGYAMSWVRQA PGKGLEWVSTISSGGTYIYY PDSVKGRFTISRDNAKNSLY LQMNSLRAEDTAVYYCARLG GDNYYEYFDVWGKGTTVTVS SGGGGSGGGGSGGGGSDIVL TQSPASLAVSPGQRATITCR ASKSVSTSGYSYMHWYQQKP GQPPKLLIYLASNLESGVPA RFSGSGSGTDFTLTINPVEA NDTANYYCQHSRELPFTFGG GTKVEIKRT | 39 |

*CDRs were determined by the Kabat method.

Third Region

In some embodiments, the hinge region comprises an amino acid sequence that has at least 95% identity to SEQ ID NO: 40. In some embodiments, the hinge region comprises an amino acid sequence that has at least 98% identity to SEQ ID NO: 40. In some embodiments, the hinge region comprises an amino acid sequence that has at least 99% identity to SEQ ID NO: 40. In some embodiments, the hinge region comprises the amino acid sequence according to SEQ ID NO: 40.

In some embodiments, the transmembrane domain comprises an amino acid sequence that has at least 95% identity to SEQ ID NO: 41. In some embodiments, the transmembrane domain comprises an amino acid sequence that has at least 98% identity to SEQ ID NO: 41. In some embodiments, the transmembrane domain comprises the amino acid sequence according to SEQ ID NO: 41. In some embodiments, the third region comprises an amino acid sequence that has at least 95% identity to SEQ ID NO: 3.

In some embodiments, the third region comprises an amino acid sequence that has at least 98% identity to SEQ ID NO: 3. In some embodiments, the third region comprises an amino acid sequence that has at least 99% identity to SEQ ID NO: 3. In some embodiments, the third region comprises the amino acid sequence according to SEQ ID NO: 3.

TABLE 4

Third Region Sequences

| Region of CAR | Description | Sequence | SEQ ID NO: |
|---|---|---|---|
| Third | hinge | KHLCPSPLFPGPSKP | 40 |
| Third | transmembrane domain | FWVLVVVGGVLACY SLLVTVAFIIFWV | 41 |

Fourth Region

In some embodiments, the costimulatory domain sequence comprises an amino acid sequence that has at least 95% identity to SEQ ID NO: 42. In some embodiments, the costimulatory domain sequence comprises the amino acid sequence according to SEQ ID NO: 42. In some embodiments, the signaling domain sequence comprises an amino acid sequence that has at least 95% identity to SEQ ID NO: 43. In some embodiments, the signaling domain sequence comprises an amino acid sequence that has at least 98% identity to SEQ ID NO: 43. In some embodiments, the signaling domain sequence comprises an amino acid sequence that has at least 99% identity to SEQ ID NO: 43. In some embodiments, the signaling domain sequence comprises the amino acid sequence according to SEQ ID NO: 43.

In some embodiments, the signaling domain sequence comprises an amino acid sequence that has at least 95% identity to SEQ ID NO: 44. In some embodiments, the signaling domain sequence comprises an amino acid sequence that has at least 98% identity to SEQ ID NO: 44. In some embodiments, the signaling domain sequence comprises an amino acid sequence that has at least 99% identity to SEQ ID NO: 44. In some embodiments, the signaling domain sequence comprises the amino acid sequence according to SEQ ID NO: 44.

In some embodiments, the fourth region comprises an amino acid sequence that has at least 95% identity to SEQ ID NO: 4. In some embodiments, the fourth region comprises an amino acid sequence that has at least 98% identity to SEQ ID NO: 4. In some embodiments, the fourth region comprises an amino acid sequence that has at least 99% identity to SEQ ID NO: 4. In some embodiments, the fourth region comprises the amino acid sequence according to SEQ ID NO: 4.

TABLE 5

Fourth Region Sequences

| Region of CAR | Description | Sequence | SEQ ID NO: |
|---|---|---|---|
| Fourth | costimulatory domain sequence | RSKRSRLLHSDYMNMTPRRPG PTRKHYQPYAPPRDFAAYRS | 42 |
| Fourth | signaling domain sequence-CD3 zeta | RVKFSRSADAPAYKQGQNQLY NELNLGRREEYDVLDKRRGRD PEMGGKPRRKNPQEGLYNELQ KDKMAEAYSEIGMKGERRGK GHDGLYQGLSTATKDTYDALH MQALPPR | 43 |
| Fourth | signaling domain sequence-CD3 zeta 1xx | RVKFSRSADAPAYKQGQNQLY NELNLGRREEYDVLDKRRGRD PEMGGKPRRKNPQEGLFNELQ KDKMAEAFSEIGMKGERRGK GHDGLFQGLSTATKDTEDALH MQALPPR | 44 |

Full Length CAR Sequences

In some embodiments, the CAR comprises an amino acid sequence that has at least 95% identity to SEQ ID NO: 45 or SEQ ID NO: 48. In some embodiments, the CAR comprises an amino acid sequence that has at least 98% identity to SEQ ID NO: 45 or SEQ ID NO: 48. In some embodiments, the CAR comprises an amino acid sequence that has at least 99% identity to SEQ ID NO: 45 or SEQ ID NO: 48. In some embodiments, the CAR comprises the amino acid sequence according to SEQ ID NO: 45 or SEQ ID NO: 48.

In some embodiments, the CAR comprises an amino acid sequence that has at least 95% identity to SEQ ID NO: 45 or SEQ ID NO: 48 and the heavy chain variable domain comprises complementarity determining regions (CDRs) HC-CDR1, HC-CDR2, and HC-CDR3, wherein the HC-CDR1, the HC-CDR2, and the HC-CDR3 comprise the amino acid sequences: HC-CDR1: SEQ ID NO: 18; HC-CDR2: SEQ ID NO: 19; HC-CDR3: SEQ ID NO: 20 and the light chain variable domain comprises complementarity determining regions (CDRs) LC-CDR1, LC-CDR2, and LC-CDR3, wherein the LC-CDR1, the LC-CDR2, and the LC-CDR3 comprise the amino acid sequences: LC-CDR1: SEQ ID NO: 21; LC-CDR2: SEQ ID NO: 22; LC-CDR3: SEQ ID NO: 23.

In some embodiments, the CAR comprises an amino acid sequence that has at least 98% identity to SEQ ID NO: 45 or SEQ ID NO: 48 and the heavy chain variable domain comprises complementarity determining regions (CDRs) HC-CDR1, HC-CDR2, and HC-CDR3, wherein the HC-CDR1, the HC-CDR2, and the HC-CDR3 comprise the amino acid sequences: HC-CDR1: SEQ ID NO: 18; HC-CDR2: SEQ ID NO: 19; HC-CDR3: SEQ ID NO: 20 and the light chain variable domain comprises complementarity determining regions (CDRs) LC-CDR1, LC-CDR2, and LC-CDR3, wherein the LC-CDR1, the LC-CDR2, and the LC-CDR3 comprise the amino acid sequences: LC-CDR1: SEQ ID NO: 21; LC-CDR2: SEQ ID NO: 22; LC-CDR3: SEQ ID NO: 23.

In some embodiments, the CAR comprises an amino acid sequence that has at least 99% identity to SEQ ID NO: 45 or SEQ ID NO: 48 and the heavy chain variable domain comprises complementarity determining regions (CDRs) HC-CDR1, HC-CDR2, and HC-CDR3, wherein the HC-CDR1, the HC-CDR2, and the HC-CDR3 comprise the amino acid sequences: HC-CDR1: SEQ ID NO: 18; HC-CDR2: SEQ ID NO: 19; HC-CDR3: SEQ ID NO: 20 and the light chain variable domain comprises complementarity determining regions (CDRs) LC-CDR1, LC-CDR2, and LC-CDR3, wherein the LC-CDR1, the LC-CDR2, and the LC-CDR3 comprise the amino acid sequences: LC-CDR1: SEQ ID NO: 21; LC-CDR2: SEQ ID NO: 22; LC-CDR3: SEQ ID NO: 23.

In some embodiments, the CAR binds to MUC1*. In some embodiments, the CAR binds to MUC1. In some embodiments, the CAR binds to MUC1* and MUC1.

Disclosed herein are nucleic acid compositions that encode any of the CARs described herein. In some embodiments, the nucleic acid sequence further comprises the sequence according to SEQ ID NO: 46.

TABLE 6

Full Length CAR Composition Sequences

| Description | Sequence | SEQ ID NO: |
|---|---|---|
| MUC1*-28zX-amino acid sequence | MALPVTALLLPLALLLHAARPEVQLVESGG GLVKPGGSLRLSCAASGFTFSGYAMSWVRQ APGKGLEWVSTISSGGTYIYYPDSVKGRFT ISRDNAKNSLYLQMNSLRAEDTAVYYCARL GGDNYYEYFDVWGKGTTVTVSSGGGGSGGG GSGGGGSDIVLTQSPASLAVSPGQRATITC RASKSVSTSGYSYMHWYQQKPGQPPKLLIY LASNLESGVPARFSGSGSGTDFTLTINPVE ANDTANYYCQHSRELPFTFGGGTKVEIKRT KHLCPSPLFPGPSKPFWVLVVVGGVLACYS LLVTVAFIIFWVRSKRSLLHSDYMNMTPR RPGPTRKHYQPYAPPRDFAAYRSRVKFSRS ADAPAYKQGQNQLYNELNLGRREEYDVLDK RRGRDPEMGGKPRRKNPQEGLFNELQKDKM AEAFSEIGMKGERRGKGHDGLFQGLSTAT KDTFDALHMQALPPR | 45 |
| WPRE Sequence | tcgacaatcaacctctggattacaaaattt gtgaaagattgactggtattcttaactatg ttgctccttttacgctatgtggatacgctg cttaatgcctttgtatcatgctattgctt cccgtatggctttcattttctcctccttgt ataaatcctggttgctgtctctttatgagg agttgtggcccgttgtcaggcaacgtggcg tggtgtgcactgtgtttgctgacgcaaccc ccactggttggggcattgccaccacctgtc agctcctttccgggacttttcgctttccccc tccctattgccacggcggaactcatcgccg cctgccttgcccgctgctggacaggggctc ggctgttgggcactgacaattccgtggtgt tgtcggggaaatcatcgtcctttccttggc tgctcgcctgtgttgccacctggattctgc gcgggacgtccttctgctacgtcccttcgg ccctcaatccagcggaccttccttcccgcg gcctgctgccggctctgcggcctcttccgc gtcttcgccttcgccctcagacgagtcgga tctcccttgggccgcctccccgcctg | 46 |
| MUC1*-8BZ-amino acid sequence | MALPVTALLLPLALLLHAARPEVQLVESGG GLVKPGGSLRLSCAASGFTFSGYAMSWVRQ APGKGLEWVSTISSGGTYIYYPDSVKGRFT ISRDNAKNSLYLQMNSLRAEDTAVYYCARL GGDNYYEYFDVWGKGTTVTVSSGGGGSGGG GSGGGGSDIVLTQSPASLAVSPGQRATITC RASKSVSTSGYSYMHWYQQKPGQPPKLLIY LASNLESGVPARFSGSGSGTDFTLTINPVE ANDTANYYCQHSRELPFTFGGGTKVEIKRT TTTPAPRPPTPAPTIASQPLSLRPEACRPA AGGAVHTRGLDFACDIYIWAPLAGTCGVLL LSLVITLYCKRGRKKLLYIFKQPFMRPVQT TQEEDGCSCRFPEEEEGGCELRVKFSRSAD APAYKQGQNQLYNELNLGRREEYDVLDKRR GRDPEMGGKPRRKNPQEGLYNELQKDKMAE AYSEIGMKGERRRGKGHDGLYQGLSTATKD TYDALHMQALPPR | 47 |

TABLE 6-continued

Full Length CAR Composition Sequences

| Description | Sequence | SEQ ID NO: |
|---|---|---|
| Mature MUC1*-28zX-amino acid sequence (without signal sequence) | EVQLVESGGGLVKPGGSLRLSCAASGFTFS GYAMSWVRQAPGKGLEWVSTISSGGTYIYY PDSVKGRFTISRDNAKNSLYLQMNSLRAED TAVYYCARLGGDNYYEYFDVWGKGTTVTVS SGGGGSGGGGSGGGGSDIVLTQSPASLAVS PGQRATITCRASKSVSTSGYSYMHWYQQKP GQPPKLLIYLASNLESGVPARFSGSGSGTD FTLTINPVEANDTANYYCQHSRELPFTFGG GTKVEIKRTKHLCPSPLFPGPSKPFWVLVV VGGVLACYSLLVTVAFIIFWVRSKRSRLLH SDYMNMTPRRPGPTRKHYQPYAPPRDFAAY RSRVKFSRSADAPAYKQGQNQLYNELNLGR REEYDVLDKRRGRDPEMGGKPRRKNPQEGL FNELQKDKMAEAFSEIGMKGERRRGKGHDG LFQGLSTATKDTFDALHMQALPPR | 48 |

Nucleic Acid Molecules

Disclosed herein are nucleic acid molecules that encode any of the CAR polypeptides described herein. In some embodiments, the nucleic acid molecule further comprises the sequence according to SEQ ID NO: 46. In some embodiments, the recombinant nucleic acid includes a nucleic acid sequence having at least 50%, at least 60%, at least 70%, at least 80%, at least 85%, at least 90%, at least 95%, at least 96%, at least 97%, at least 98%, at least 99%, or 100% sequence identity sequence identity to a nucleic acid sequence according to SEQ ID NO: 46.

In some embodiments, the recombinant nucleic acid molecule is further defined as an expression cassette or a vector. It can be understood that an expression cassette generally includes a construct of genetic material that contains coding sequences and enough regulatory information to direct proper transcription and/or translation of the coding sequences in a recipient cell, in vivo and/or ex vivo. Generally, the expression cassette may be inserted into a vector for targeting to a desired host cell and/or into an individual. As such, in some embodiments, an expression cassette of the disclosure includes a coding sequence for the CAR polypeptide as disclosed herein, which is operably linked to expression control elements, such as a promoter, and optionally, any other sequences or a combination of other nucleic acid sequences that affect the transcription or translation of the coding sequence.

In some embodiments, the nucleotide sequence is incorporated into an expression vector. It can be understood by one skilled in the art that the term "vector" generally refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector.

In some embodiments, the expression vector can be a viral vector. As can be appreciated by one of skill in the art, the term "viral vector" can refer either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. In some embodiments, the vector is a vector derived from a lentivirus, an adeno virus, an adeno-associated virus, a baculovirus, or a retrovirus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

In some embodiments, the nucleic acid sequences encoding the CAR polypeptides can be optimized for expression in the host cell of interest. For example, the G-C content of the sequence can be adjusted to average levels for a given cellular host, as calculated by reference to known genes expressed in the host cell. Methods for codon usage optimization are known in the art. Codon usages within the coding sequence of the chimeric receptor disclosed herein can be optimized to enhance expression in the host cell, such that about 1%, about 5%, about 10%, about 25%, about 50%, about 75%, or up to 100% of the codons within the coding sequence have been optimized for expression in a particular host cell.

The nucleic acid molecules provided can contain naturally occurring sequences, or sequences that differ from those that occur naturally, but, due to the degeneracy of the genetic code, encode the same polypeptide, e.g., antibody for the ECD. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies for the ECD); some or all of the non-coding sequences that lie upstream or downstream from a coding sequence (e.g., the coding sequence of a chimeric receptor) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Cell Compositions Containing a CAR Composition

Disclosed herein are cell compositions comprising a CAR according to any of the above embodiments. In some embodiments, the cell is an immune cell. In some embodiments, the cell is a T-cell, a natural killer cell, a dendritic cell, or a mast cell. In some embodiments, the cell is derived from a patient or from a donor. In some embodiments, the cell remains active at least 30 days after administration to a patient. In some embodiments, the cell remains active at least 60 days after administration to a patient. In some embodiments, the cell remains active at least 90 days after administration to a patient, which can prevent tumor recurrence.

The nucleic acid molecules of the present disclosure can be introduced into a cell (i.e., a host cell), such as a human T cell, to produce a recombinant cell containing the nucleic acid molecule. Accordingly, some embodiments of the disclosure relate to methods for making a recombinant cell, including (a) providing a host cell capable of protein expression; and transducing the provided host cell with a recombinant nucleic acid of the disclosure to produce a recombinant cell. Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be introduced into a host cell by viral or non-viral delivery vehicles known in the art to produce an engineered cell. For example, the nucleic acid molecule can be stably integrated in the host genome, or can be episomally replicating, or present in the recombinant host cell as a mini-circle expression vector for a stable or transient expression. Accordingly, in some embodiments disclosed herein, the nucleic acid molecule is maintained and replicated in the recombinant host cell as an episomal unit. In some embodiments, the nucleic acid molecule is stably integrated into the genome of the recombinant cell. Stable integration can be completed using classical random genomic recombination techniques or with more precise genome editing techniques such as using zinc-finger proteins (ZNF), guide RNA directed CRISPR/Cas9, DNA-guided endonuclease genome editing NgAgo (Nalronobacleriiim gregoryi Argonaute), or TALEN genome editing (transcription activator-like effector nucleases).

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, baculoviral virus or adeno-associated virus (AAV) can be engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g. transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the CAR polypeptides of interest.

As outlined above, some embodiments of the disclosure relate to various methods for making a recombinant cell, including (a) providing a host cell capable of protein expression; and transducing the provided host cell with a recombinant nucleic acid of the disclosure to produce a recombinant cell. Non-limiting exemplary embodiments of the disclosed methods for making a recombinant cell can further include one or more of the following features. In some embodiments, the host cell is obtained by leukapheresis performed on a sample obtained from a subject, and the cell is transduced ex vivo. In some embodiments, the recombinant nucleic acid is encapsulated in a viral capsid or a lipid nanoparticle. In some embodiments, the methods further include isolating and/or purifying the produced cells. Accordingly, the recombinant cells produced by the methods disclosed herein are also within the scope of the disclosure.

Techniques for transforming a wide variety of the above-mentioned host cells and species are known in the art and described in the technical and scientific literature. For example, DNA vectors can be introduced into eukaryotic cells via conventional transformation or transfection techniques. Suitable methods for transforming or transfecting cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection. In some embodiments, the nucleic acid molecule is introduced into a host cell by a transduction procedure, electroporation procedure, or a biolistic procedure. Accordingly, cell cultures including at least one recombinant cell as disclosed herein are also within the scope of this application.

Pharmaceutical Compositions

In some embodiments, the cell is in a saline solution comprising human serum albumin. In some embodiments, the cell is in an infusible cryopreservation solution. In some embodiments, the infusible cryopreservation solution comprises one or more of sodium, potassium, magnesium, chloride, acetate, or gluconate. In some embodiments, the infusible cryopreservation solution comprises 140 mEq sodium, 5 mEq potassium, 3 mEq magnesium, 98 mEq chloride, 27 mEq acetate, and 23 mEq gluconate. In some embodiments, the infusible cryopreservation solution comprises human serum albumin (HSA) at a concentration range of 2% to 5%. In some embodiments, the infusible cryopreservation solution comprises human serum albumin (HSA) at a final concentration of 2.5%. In some embodiments, the infusible cryopreservation solution has a pH from 7.0 to 7.5. In some embodiments, the infusible cryopreservation solution has a pH of 7.4. In some embodiments, the infusible cryopreservation solution comprises dimethyl sulfoxide (DMSO). In some embodiments, the infusible cryopreservation solution comprises 2% to 5% (w/v) dimethyl sulfoxide (DMSO). In some embodiments, the infusible cryopreservation solution comprises 5% (w/v) dimethyl sulfoxide (DMSO).

Methods of Treatment

Disclosed herein are methods of treating cancer comprising administering one or more cells expressing the CAR of any of claims 1-11 to a subject in need thereof. In some embodiments, the at least 300,000 to 1,000,000,0000 of the cells expressing the CAR of any of claims 1-11 are administered to the subject.

Disclosed herein are methods of treating cancer comprising administering one or more first cells comprising a first chimeric antigen receptor and also administering one or more second cells comprising a second chimeric antigen receptor, wherein the first cells express the CAR of any of claims 1-11 to a subject in need thereof.

Disclosed herein are methods of treating cancer comprising administering one or more first cells comprising a first chimeric antigen receptor and subsequently administering one or more second cells comprising a second chimeric antigen receptor, wherein the second chimeric antigen receptor comprises an amino acid sequence with at least 90% identity to SEQ ID NO: 47 to a subject in need thereof.

In some embodiments, the second chimeric antigen receptor comprises an amino acid sequence with at least 95% identity to SEQ ID NO: 47 to a subject in need thereof.

In some embodiments, the second chimeric antigen receptor comprises the amino acid sequence according to SEQ ID NO: 47 to a subject in need thereof.

In some embodiments, the at least 300,000 to 1,000,000,0000 of the first cells are administered to the subject.

In some embodiments, the at least 300,000 to 1,000,000,0000 of the second cells are administered to the subject.

In some embodiments, the cancer expresses MUC1. In some embodiments, the cancer expresses MUC1*. In some embodiments, the cancer is MMP9 positive. In some embodiments, the cancer is breast cancer, colon cancer, prostate cancer, pancreatic cancer, or lung cancer. In some embodiments, the breast cancer is HER2−/ER+/PR−, or HER2−/ER+/PR+, or HER2−/ER−/PR+, or HER2+, or HER2+/PR+/ER−, HER2+/ER+/PR−, or triple negative breast cancer. In some embodiments, the breast cancer is HER2−/ER+/PR−. In some embodiments, the breast cancer is HER2−/ER+/PR+. In some embodiments, the breast cancer is HER2−/ER−/PR+. In some embodiments, the breast cancer is HER2+/PR+/ER−. In some embodiments, the breast cancer is HER2+/ER+/PR−. In some embodiments, the breast cancer is triple negative breast cancer.

In some embodiments, the method further comprises administration of an anti-cancer agent. In some embodiments, the anti-cancer agent comprises a cytotoxic agent. In some embodiments, the cytotoxic agent comprises a platinum-based agent or a taxane. The platinum-based agent is carboplatin or cisplatin. The taxane is paclitaxel or docetaxel.

Articles of Manufacture

In another aspect of the disclosure, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic.

The label or package insert indicates that the composition is used for treating the condition of choice. The article of manufacture in this embodiment of the disclosure may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Definitions

The terminology used herein is for the purpose of describing particular cases only and is not intended to be limiting. As used herein, the singular forms "a" "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "antibody" is used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2: 106 (1991); Courtenay-Luck, "Genetic Manipulation of Monoclonal Antibodies," in Monoclonal Antibodies: Production, Engineering and Clinical Application, Ritter et al. (eds.), pages 166-179 (Cambridge University Press 1995); and Ward et al., "Genetic Manipulation and Expression of Antibodies," in Monoclonal Antibodies: Principles and Applications, Birch et al., (eds.), pages 137-185 (Wiley-Liss, Inc. 1995).

In some instances, the CDRs of an antibody are determined according to (i) the Kabat numbering system (Kabat et al. (1971) Ann. NY Acad. Sci. 190:382-391 and, Kabat et al. (1991) Sequences of Proteins of Immunological Interest Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1): 175-82; and U.S. Pat. No. 7,709,226); or (iii) the ImMunoGeneTics (IMGT) numbering system, for example, as described in Lefranc, M.-P., 1999, The Immunologist, 7: 132-136 and Lefranc, M.-P. et al, 1999, Nucleic Acids Res., 27:209-212 ("IMGT CDRs"); or (iv) MacCallum et al, 1996, J. Mol. Biol., 262:732-745. See also, e.g., Martin, A., Protein Sequence and Structure Analysis of Antibody Variable Domains, in Antibody Engineering, Kontermann and Dübel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35 A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, the term "percent (%) amino acid sequence identity" or "percent (%) identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "individual(s)", "subject(s)" and "patient(s)" are used interchangeably herein and refer to any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Provided herein are exemplary experiments, procedures and findings on MUC1*-28zX, a successor to MUC1*-8BZ. MUC1*-28zX overcomes two major challenges to the effective use of chimeric antigen receptor T cell therapies (CAR) T cell therapy for solid tumor cancers: (1) CAR T cell exhaustion; and 2) inability to recognize and kill low antigen-expressing tumor cells, which are characteristic of early-stage cancers.

As disclosed here, studies demonstrate that T cells expressing MUC1*-28zX demonstrated greatly increased persistence and ability to recognize and kill tumor cells expressing low to medium amounts of the antigen. MUC1*-28zX T cells are also effective against cancer cells with high MUC1* expression, which are characteristic of late-stage cancers. Additionally, in vitro studies of MUC1*-28zX T cells in co-culture with normal cells expressing full-length MUC1 showed no evidence of T cell activation and essentially no killing of the normal cells.

Example 1: Chimeric Antigen Receptors Targeting MUC1*

The three chimeric antigen receptors (CARs) evaluated in these examples share a common humanized single chain antibody (scFv) domain, huC2, derived from the C2 antibody specific for MUC1*. In MUC1*-8BZ, huC2 is linked to hinge and transmembrane regions derived from CD8, a costimulatory domain derived from 4-1BB, and a signaling domain derived from CD3ζ (CD3z) (FIG. 1A). MUC1*-28Z is similar to MUC1*-8BZ, but has hinge, transmembrane and costimulatory domains derived from CD28 (FIG. 1B). MUC1*-28zX is identical to MUC1*-28Z except the second and third ITAM motifs of the CD3z signaling domain each have two Tyr to Phe mutations, as described for the 1XX mutants of WO2019133969 (FIG. 1C). DNA sequences encoding the three CARs were inserted into a lentiviral vector containing an MSCV promoter (Lentigen, Miltenyi) for expression in immune cells.

Example 2: MUC1* Expression in Xenograft Tumors

MUC1* expression was quantified by staining tumors with the C2 antibody and determining an H-score, as described by Meyerholz and Ram. See Meyerholz D. K. and Beck A. P., Principles and approaches for reproducible scoring of tissue stains in research. Lab Invest, 2018. 98(7): p. 844-855; Ram S, Vizcarra P, Whalen P, Deng S, Painter C L, Jackson-Fisher A, et al. (2021) Pixelwise H-score: A novel digital image analysis-based metric to quantify membrane biomarker expression from immunohistochemistry images. PLoS ONE 16(9): e0245638. MUC1* expression is quantified on a scale of 0, 1, 2, or 3 in different regions of a tumor section, and the percentage of the tumor having each expression level is determined. The H-score is then calculated by summing (percentage×expression level) at each expression level. The maximum possible H-score is 300. Early tumors typically have a lower H-score. High H scores are a characteristic of early cancers, whereas later stage cancers are characterized by low H scores.

Xenograft tumors were generated by subcutaneous injection of cancer cells from cell lines representative of various cancer types into nude NOD/SCID/GAMMA (NSG) mice. In some instances, the cancer cells were engineered to overproduce MUC1*. Tumors were excised from the mice for H-score analysis when a pathologist determined that the tumor burden was excessive.

HCT-116 human colon cancer cells that had been transfected to express MUC1* and a luciferase reporter (HCT-MUC1*).

TABLE 7

MUC1* expression in xenograft tumors derived from human cancer cell lines as determined by H-score analysis

| Cancer Type | Cell Line | Excision Day | H-Score |
| --- | --- | --- | --- |
| Breast | T47D-WT | 100 | 10 |
| Breast | T47D-MUC1* | 20-25 | 280 |
| Breast | T47D with 30% MUC1* | 20-25 | 80 |
| Breast | T47D with 15% MUC1* | 20-25 | 40 |
| Breast | T47D with 7.5% MUC1* | 20-25 | 30 |
| Lung | NCI-H1975 | 20-25 | 40 |
| Pancreas | HPAF.II | 20-25 | 200 |
| Colon | HCT-116 | 20-25 | 0 |

Example 3: Increased Persistence of MUC1*-28zX CAR T Cells

Figure 2:
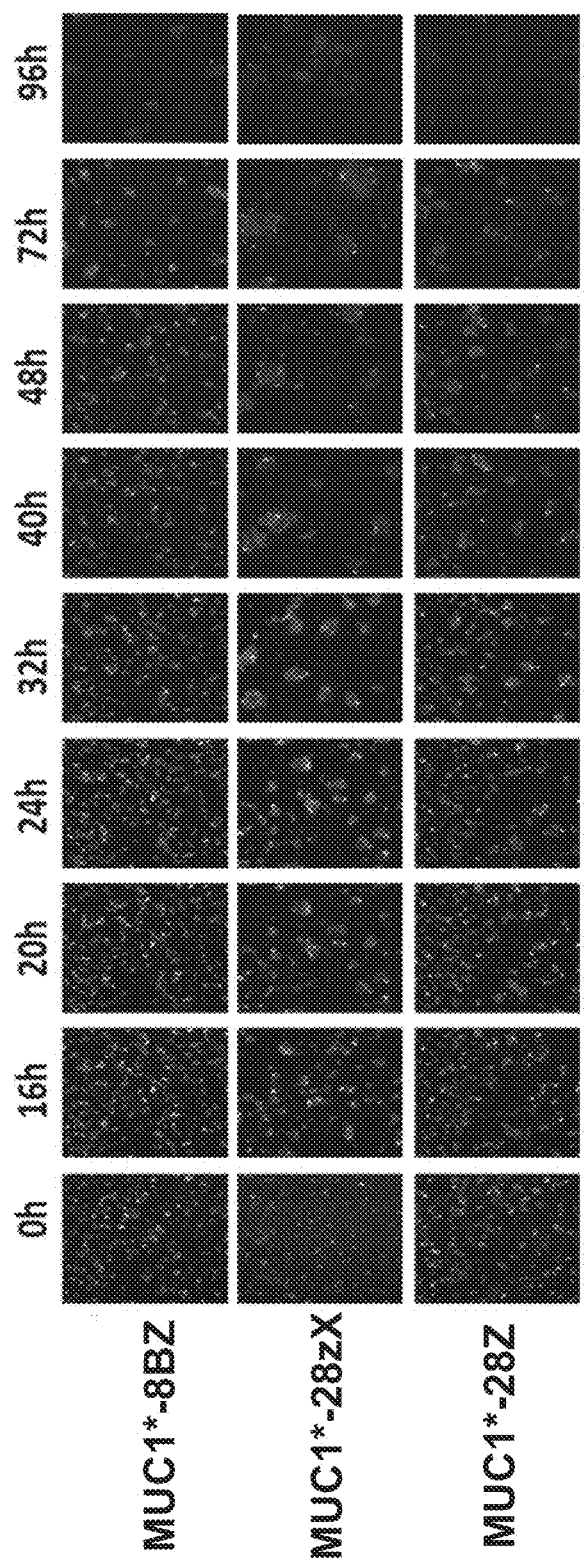
FIG. 2 illustrates the effects of continuous target antigen stimulation on the cytotoxic activity of anti-MUC1* CAR T cells. CAR T cells were pre-incubated for 4 days with magnetic beads presenting a synthetic MUC1* peptide and then added to a mixed population of T47D cells in which 15% of the T47D cells were engineered to express high levels of MUC1* (T47D-MUC1*). The images show cells expressing GFP (high MUC1* expression), mCherry (all T47D cells) and stained with Caspase 3 to identify dead cells (blue). MUC1*-28zX CAR T cells had greater persistence after pre-stimulation with MUC1* beads and were capable of killing T47D cells with low/wild-type MUC1* expression.

CAR T cells expressing MUC1*-28zX, MUC1*-28Z, or MUC1*-8BZ were incubated with magnetic beads presenting a synthetic MIUC1* peptide (SEQ ID NO: 49) to simulate repeated CAR T stimulation and activation by the target antigen. After 6 days, the magnetic beads were removed and the pre-stimulated CAR T cells were co-cultured for 96 hours with a heterologous population of T47D breast cancer target cells expressing mCherry. 15% of the target cells were engineered to express high levels of MUC1* and also expressed a GFP marker. The remaining 85% of the target cells expressed low (wild-type) levels of MUC1*. After 96 hours of pre-stimulation, the MUC1*-28zX CAR T cells killed the target cells faster than the MUC1*-28Z or MUC1*-8BZ CAR T cells, demonstrating increased persistence (FIG. 2). Furthermore, the MUC1*-28zX CAR T cells had cytotoxic activity against T47D cells expressing low levels of MUC1*, whereas the MUC1*-28Z or MUC1*-8BZ CART cells could only kill the GFP positive T47D cells expressing high MUC1*. CAR T cells expressing MUC1*-28zX, MUC1*-28Z also remained active after stimulation with a fragment of the peptide comprising SEQ ID NO: 49 lacking 10 N-terminal amino acids.

Figure 3A:
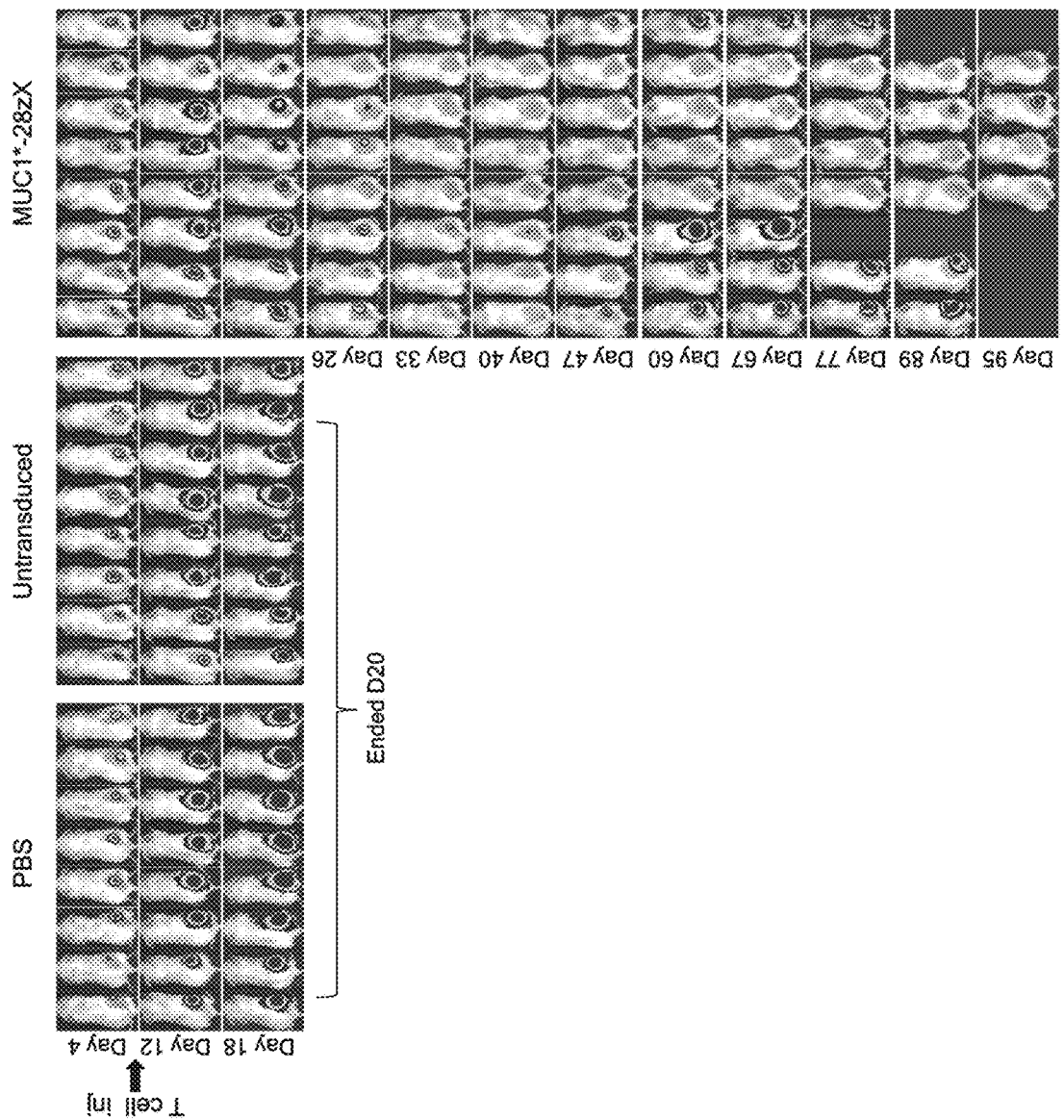
FIG. 3A presents bioluminescence images of colon cancer xenograft tumors in NSG mice treated with PBS buffer, untransduced T cells, or MUC1*-28zX CAR T cells.
Figure 3B:
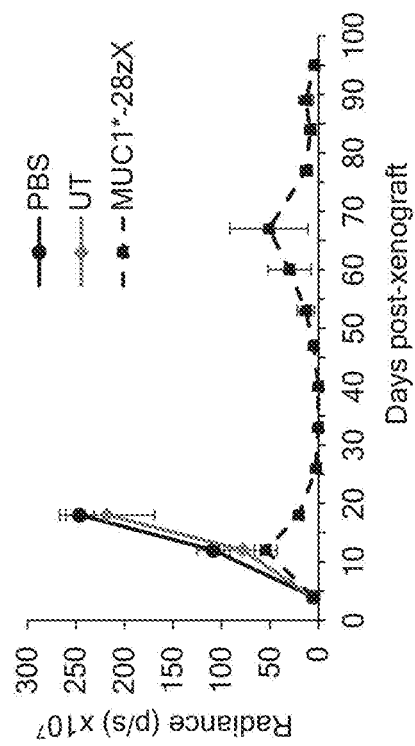
FIG. 3B is a graph quantifying bioluminescence in the NSG mice. The MUC1*-28zX CAR T cells cleared the tumors by day 26.

Example 4: Persistent Shrinkage of Colon Cancer Tumors by MUC1*-28zX CAR T Cells A colon cancer xenograft system was used to test the in vivo efficacy and persistence of MUC1*-28zX T cells. Tumors were generated in NSG mice by subcutaneous injection of HCT-116 human colon cancer cells that had been transfected to express MUC1* and a luciferase reporter (HCT-MUC1*). The parental HCT-116 cells are MUC1* negative, so MUC1* was ectopically expressed to render the cells susceptible to killing by CAR T cells with an anti-MUC1* targeting domain. The luciferase allows luminescence from the tumors to be detected using an IVIS instrument. The MUC1* expression vector carries a GFP reporter, and the luciferase expression vector carries an mCherry reporter. 500K HCT-MUC1* cancer cells were subcutaneously injected into a flank of female NSG mice. After allowing tumor formation and growth for five days, 10M CAR T cells (E:T of 20:1) were injected into the tail vein, and changes in tumor mass were monitored by IVIS (FIGS. 3A-3B).

In controls treated with PBS buffer or untransduced T cells, the mice had to be sacrificed before Day 26 due to their massive tumor burden. In contrast, the MUC1*-28zX CAR T cells cleared the HTC-MUC1* tumors by Day 26. Half of the mice treated with MUC1*-28zX CAR T cells remained tumor free until the end of the experiment on Day 95. The tumors that recurred in other mice were MUC1* negative, suggesting that their Muc*transgene had been silenced or lost. These results demonstrate that MUC1*-28zX CAR T cells have cytotoxic activity against MUC1* positive human colon cancer cells and that this activity persists for at least 90 days and suppresses tumor recurrence. Increased persistence is important because clinical experience with CAR T cell therapies has revealed that cancer remissions are brief in a substantial number of patients owing to poor CAR T cell persistence. Shah and Fry, Nat Rev Clin Oncol. 2019 June; 16(6): 372-385.

Figure 4:
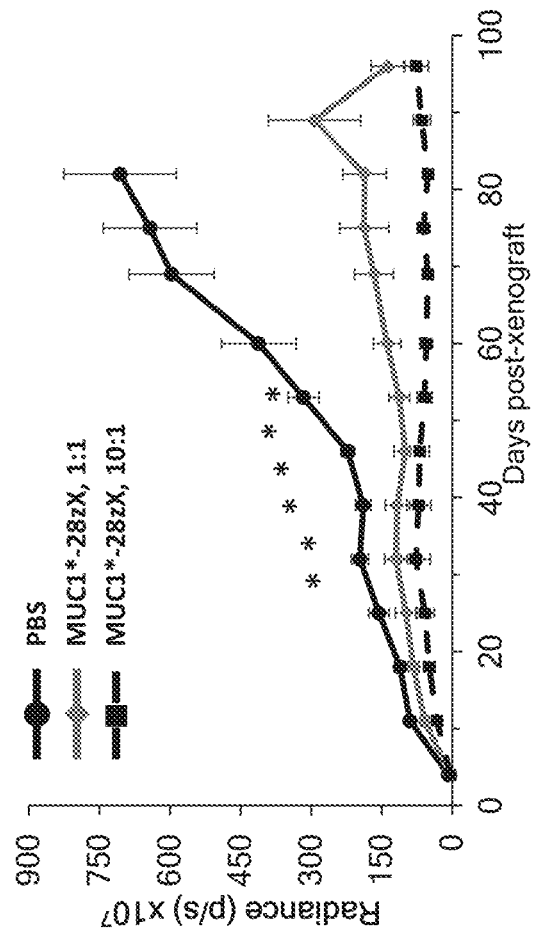
FIG. 4 is a graph quantifying bioluminescence of T47D breast cancer xenografts with low MUC1* expression in NSG mice after treatment with PBS buffer, 250K MUC1*-28zX CAR T cells or 2.5M MUC1*-28zX CAR T cells.

Example 5: MUC1*-28zX Treatment of Breast Cancer Tumors with Low MUC1* Expression The efficacy of MUC1*-28zX for treating breast cancer was investigated using T47D cells from a naturally-occurring human breast cancer that express low to medium amounts of MUC1*. Female NSG mice were implanted with 90-day estrogen pellets followed by subcutaneous injection of 250K T47D cells expressing luciferase. The mice were treated with MUC1*-28zX CAR T cells on Day 5 at an effector:target ratio of 1:1 (250K CAR T cells) or 10:1 (2.5M CAR T cells). Tumor growth was monitored by IVIS. Both doses substantially inhibited tumor growth over 96 days when compared to a PBS control (FIG. 4). These results demonstrate that MUC1*-28zX CAR T cells have in vivo cytotoxic activity against human breast cancer cells with low MUC1* expression and that this activity persists for at least 91 days. CAR T activity on cancer cells with low expression of the target antigen is important because insufficient reactivity against cells with low antigen density has emerged as an important cause of CAR resistance. Majzner et. al., Cancer Discov. 2020 May; 10(5): 702-723. Improved cytotoxicity on low antigen target cells by a CAR having ITAM mutations in its CD3 signaling domain was surprising because a previous study concluded that the number of ITAM domains in a CAR should be increased to enhance signal strength and enable recognition of low antigen density cells, while ITAM mutations blunt signal and increase the antigen density threshold. Id.

Example 6: MUC1*-28zX Treatment of Breast Cancers with Heterologous MUC1* Expression Natural tumors are often comprised of cancer cells expressing heterogeneous amounts of MUC1* (WO2020146902). To model natural tumors, T47D breast cancer cells expressing low to medium amounts of MUC1* were mixed with transgenic T47D-MUC1* cells with high MUC1* expression. All of the T47D cells were transfected with a luciferase-mCherry expression vector to track tumor cells. The T47D-MUC1* cells were transfected with a Muc1*-GFP transgene to permit identification of by GFP fluorescence.

To investigate T cell persistence during the treatment of tumors with heterologous MUC1* expression, a total of 250K T47D cells consisting of 7.5%, 15%, or 30% T47D-MUC1* (high antigen) cells in a background of T47D-wt (low-medium antigen) cells were subcutaneously injected into female NSG mice that had previously been implanted with 90-day estrogen release pellets. Five days later, the animals were intravenously injected with either 250K or 2.5M (E:T ratio of 1:1 or 10:1) human T cells that had been transduced with MUC1*-28zX, MUC1*-8BZ, or MUC1*-28Z, or a PBS buffer control.

Figure 5:
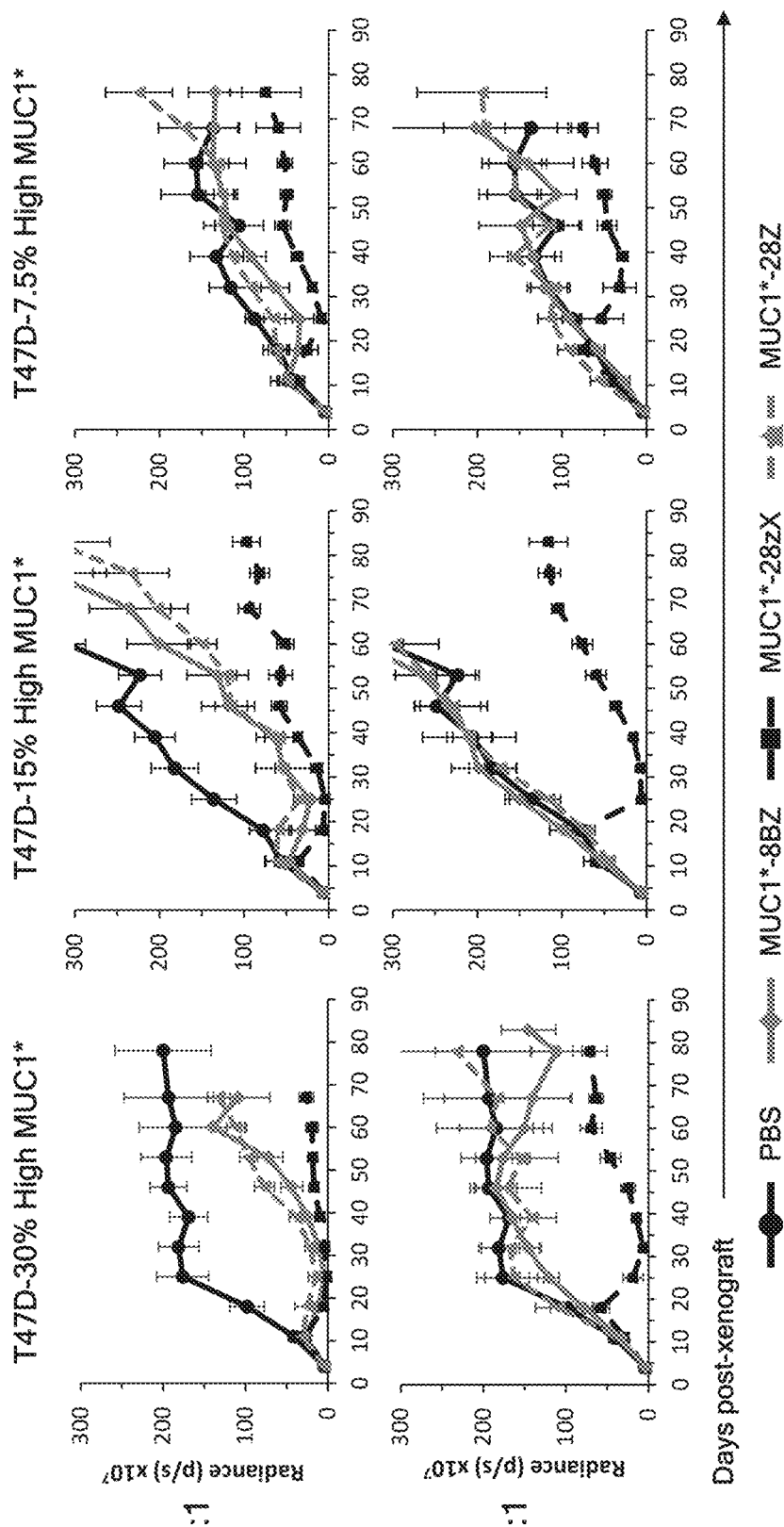
FIG. 5 shows graphs quantifying bioluminescence of T47D breast cancer xenografts in NSG mice after administration of PBS buffer, MUC1*-8BZ CAR T cells, MUC1*-28Z-3z CAR T cells, or MUC1*-28zX CAR T cells. The CAR T cells were administered on Day 0 at effector-to-target ratios of 10:1 or 1:1. The xenografts were generated from populations of T47D wild-type cells mixed with the indicated percentages of T47D-MUC1* cells with high MUC1* expression.

Bioluminescence measurements of the T47D tumors shows that both doses of MUC1*-28zX CAR T cells inhibited the growth of T47D tumors regardless of the percentage of T47D-MUC1* cells, and did so more effectively than MUC1*-8BZ or MUC1*-28Z CAR T cells under all conditions tested. MUC1*-28zX inhibited tumor recurrence, whereas in animals treated with MUC1*-8BZ or MIUC1*-28Z CAR T, tumors recurred around Day 40-50 post tumor implantation. FIG. 5. The increased efficacy of MUC1*-28zX CAR T cells was most apparent at the lower dose (1:1 effector:target ratio), when each CAR T cell would have to act on multiple target cells. The lower dose would be expected to lead to CAR T cell exhaustion (taking into account the uncontrolled tumor growth occurring before and shortly after intravenous CAR T administration). The MUC1*-8BZ and MUC1*-28Z CAR T cells performed best at the higher dose (10:1 effector:target ratio) against T47D tumors having 30% high expressing T47D-MUC1* cells. Under these less stringent conditions, they inhibited tumor growth almost as well as MUC1*-28zX CAR T cells until Day 39, when their efficacy declined and tumors recurred. In contrast, MUC1*-8BZ and MUC1*-28Z CAR T cells performed no better than the PBS control when administered at the lower dose.

Figure 6:
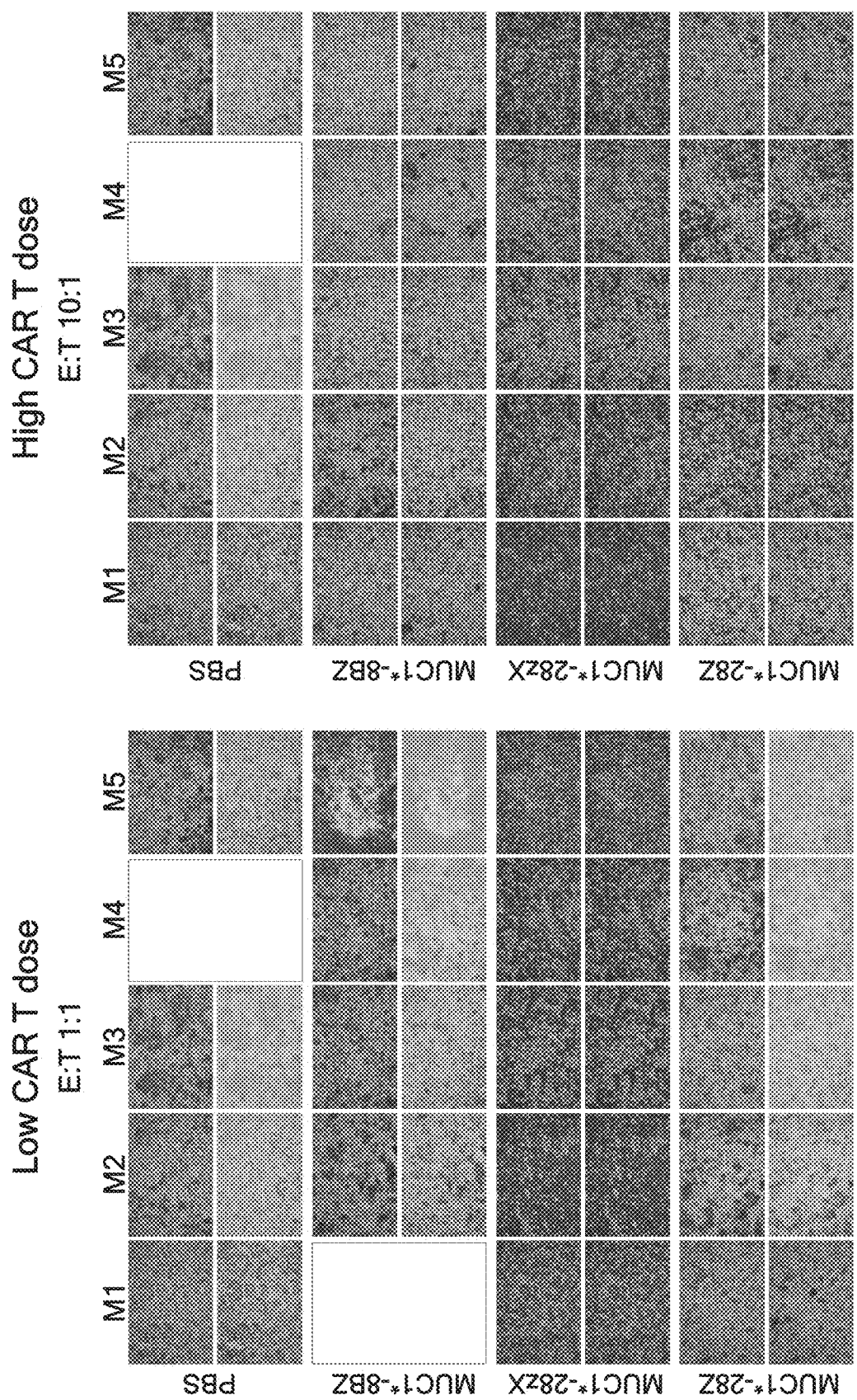
FIG. 6 presents microscopic images of tumor tissues excised from mice (M1-M5 for each condition) after treatment with low (1:1) or high (10:1) effector-to-target ratios of the indicated CAR T cells or a PBS control. The upper panels for each treatment show mCherry positive (red) T47D cells overlayed on a phase image, and the lower panels show GFP positive (green) T47D-MUC1* cells overlayed on the phase image.

Results for the PBS control mice show that tumors with a higher percentage of high-expressing T47D-MUC1* cells had a higher growth rate, indicating that high expression of the MUC1* growth factor receptor contributes to tumor virulence. Likewise, immunofluorescent images from tumors at the end of the experiment revealed that untreated tumors were dominated by GFP positive T47D-MUC1* cells with high MUC1* expression (FIG. 6). In contrast, GFP positive cells were depleted in the late-growing tumors observed in mice treated with the higher dose of MUC1*-8BZ and MUC1*-28Z CAR T cells, suggesting that anti-MUC1* CARs with a wild-type CD3z signaling domain are most effective against the high-MUC1* target cells. Surprisingly, the MIUC1*-28zX CAR T cells eliminated both the high MUC1* expressing GFP-positive T47D-MUC1* cells and the low MIUC1* expressing mCherry only T47D wild-type cells. These results indicate that the MUC1*-28zX CAR having reduced CD3z signaling provides two important advantages over anti-MUC1* CARs with normal CD3z signaling: (1) enhanced cytotoxicity against cancer cells with low MUC1* expression and (2) increased persistence and suppression of tumor recurrence.

Figure 7:
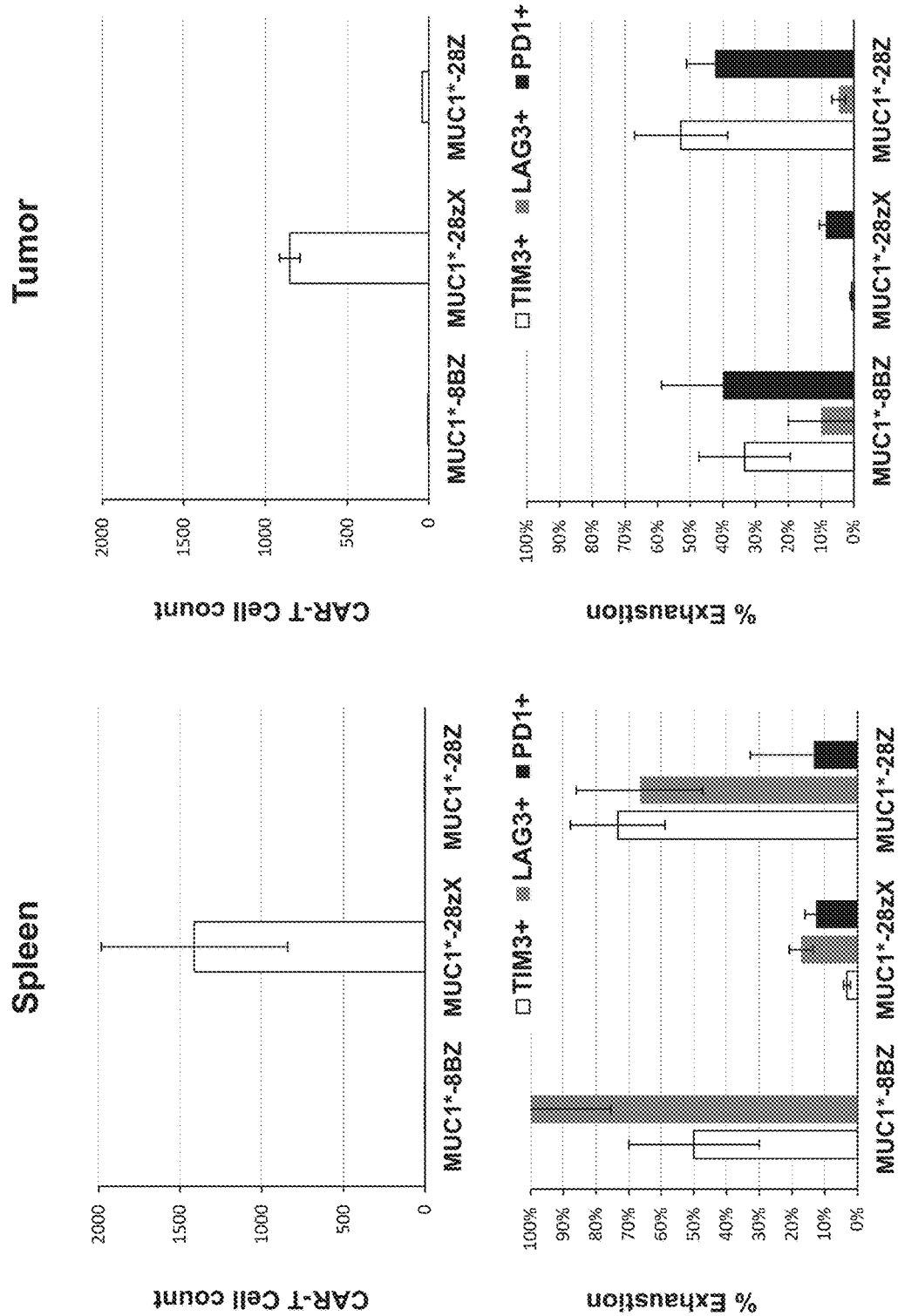
FIG. 7 presents graphs showing numbers of CAR T cells extracted from blood, spleen and tumor and percentages of extracted CAR T cells expressing the indicated T cell exhaustion markers for the mice in FIG. 6.

CAR T cells were recovered from the blood, spleen and tumors of the mice at the end of the experiment to investigate the mechanism underlying the improved performance of the MIUC1*-28zX CAR. Under conditions where the MUC1*-28zX CAR most strongly outperformed the CARs with a wild-type CD3z domain (1:1 effector:target ratio, 7.5% T47D-MUC1* cells), the number CAR T cells recovered from each sample was higher and the percentage of recovered CAR T cells displaying molecular markers of T cell exhaustion (TIM3, LAG3, and PD-1) was lower for MUC1*-28zX (FIG. 7).

The maturation status of CAR T cells was determined by flow cytometry. Cells were stained with an antibody against human CD3 to identify transplanted T cells, the FAB2' antibody to detect CAR expression, and antibodies against CD62L and CD45RO to determine T cell maturation status. Naïve T cells are CD62L positive and CD45RO negative. Central memory T cells (CM) are CD62L positive and CD45RO positive. Effector memory T cells (EM) are CD62L negative and CD45RO positive. Effector T cells are CD62L negative and CD45RO negative.

In mice with T47D human breast cancer tumors, the percentage of CAR T cells that were in the effector state on Day 69 after tumor implantation was higher for MUC1*-28zX than for MUC1*-8BZ (Table 8). The percentage MUC1*-28zX CAR T cells that were in the effector state doubled when the amount of MUC1* expressed by the tumors was increased (compare T47D-WT versus T47D-MUC1*). In contrast, higher MUC1* expression had no effect on the percentage of MUC1*-8BZ CAR T cells that progressed to the effector state. Additionally, 68% of the MUC1*-28zX CAR T cells recovered from mice on Day 93-96 post treatment were CD8 positive cells with cytotoxic activity. These results demonstrate that MUC1*-28zX CAR T cells were more strongly activated for killing the MUC1* positive tumors and were capable of responding to elevated MUC1* expression by the tumor.

TABLE 8

Maturation status of CAR T cells isolated from mice with breast cancer tumors

| | MUC1*-28zX | | MUC1*-8BZ | |
| --- | --- | --- | --- | --- |
| | T47D-WT | T47D-MUC1* | T47D-WT | T47D-MUC1* |
| Eff | 14.4 | 29.8 | 8.1 | 8.2 |
| Naïve | 2.5 | 1.6 | 2.3 | 0.4 |
| CM | 8.8 | 3.2 | 7.9 | 13.8 |
| EM | 74.3 | 65.3 | 81.7 | 77.6 |

Values indicate the percentage of total CAR T cells, n = 5

To monitor maturation of MUC1*-28zX CAR T cells over time, blood was collected from CAR T treated mice on days 20 and 60 after tumor implantation. In this experiment, 15% of the T47D breast cancer cells had elevated MUC1* expression and the MUC1*-28zX CAR T cells were administered on Day 6 at two different doses (effector to target ratios of 1:1 or 10:1). With both doses, the percentage of CAR T cells that were naïve T cells increased from Day 20 to Day 60, further supporting the persistence of MUC1*-28zX CAR T cells. In addition, the percentages of central memory (CM) and effector memory (EM) cells were reduced. These results demonstrate that a reservoir of naïve MUC1*-28zX CAR T cells is available to prevent recurrence of the MUC1* positive tumors.

TABLE 9

Maturation status of MUC1*-28zX CAR T cells isolated from the blood of mice with T47D human breast cancer tumors

| E:T Ratio | Day | Naïve | CM | EM | Eff |
|---|---|---|---|---|---|
| 1:1 | 20 | 15 ± 10 | 3.7 ± 3.2 | 5.0 ± 4.4 | 76 ± 54 |
|  | 69 | 27 ± 13 | 0.0 | 0.0 | 73 ± 33 |
| 10:1 | 20 | 20 ± 4 | 6.0 ± 0.8 | 6.7 ± 2.0 | 67 ± 11 |
|  | 69 | 36 ± 6 | 0.4 ± 0.3 | 0.4 ± 0.2 | 63 ± 16 |

Values indicate the percentage of total CAR T cells ± SEM, n = 5

Example 7. MUC1*-28zX Treatment of Lung Cancers

Figure 8:
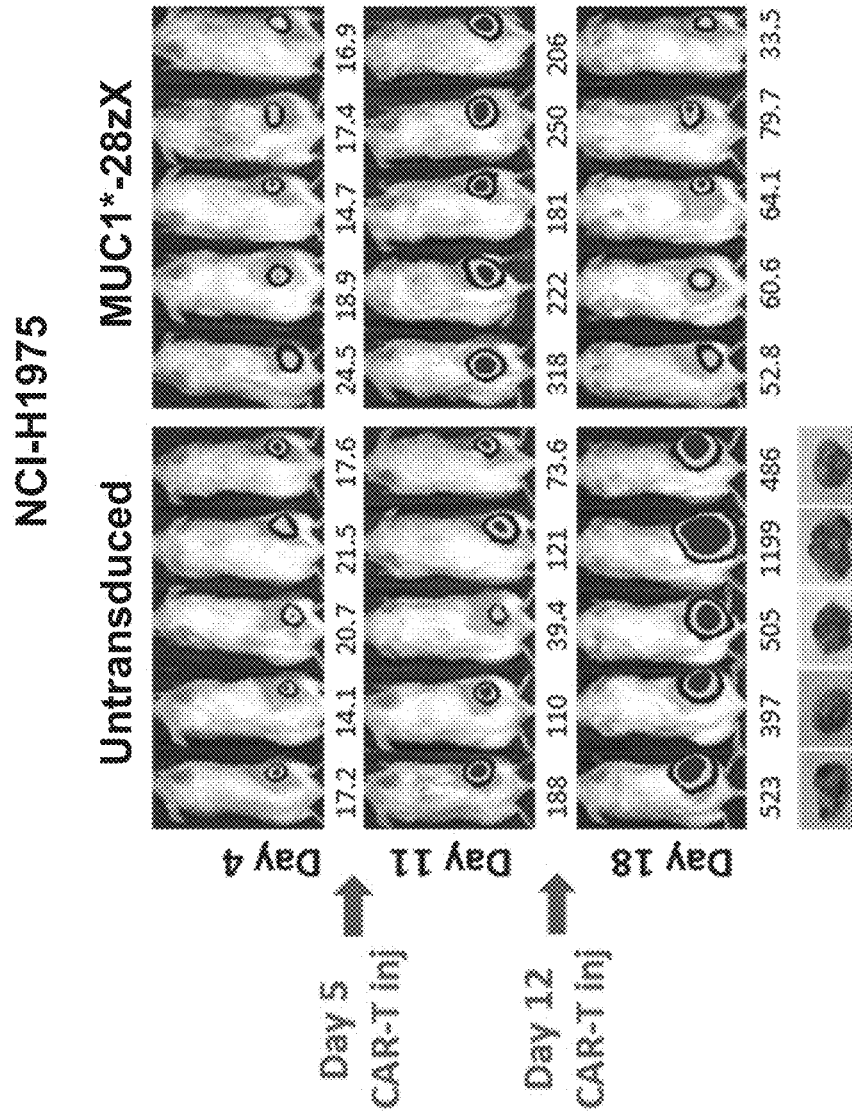
FIG. 8 presents bioluminescence of human NCI-H1975 non-small cell lung cancer xenografts treated with 20M untransduced T cells or 20M MUC1*-28zX CAR T cells. The T cells were intravenously administered at a 10:1 effector-to-target cell ratio on Day 5 and Day 12 post-tumor implantation. Tumor volume was substantially reduced in the mice treated with the MUC1*-28zX CAR T cells.

NCI-H1975 non-small cell lung cancer cells were implanted into NSG mice. On Day 5 and Day 12 post implantation, MUC1*-28zX or untransduced T cell generated from the same donor were intravenously administered at a 10:1 effector to target cell ratio Bioluminescent photographs taken at Day 18 show a 10-30 fold reduction in tumor volume with MUC1*-28zX T cells (FIG. 8). Control animals had to be sacrificed at Day 18 due to excessive tumor burden. These results demonstrate that MUC1*-28zX T cells targeting MUC1* are effective for the treatment of lung cancers.

Example 8. MUC1*-28zX Treatment of Pancreatic Cancers

Figure 9:
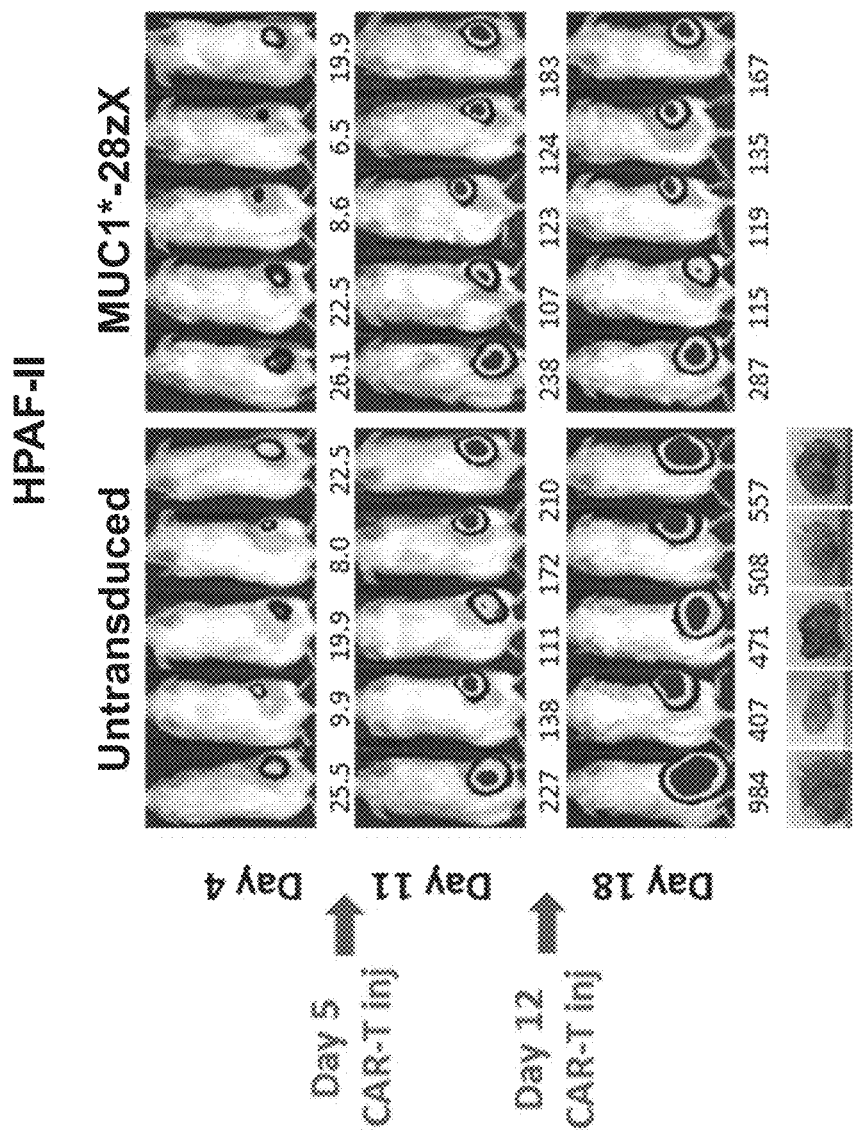
FIG. 9 presents bioluminescence of human HPAF-II pancreatic cancer cells xenografts treated with untransduced T cells or MUC1*-28zX CAR T cells. The T cells were intravenously administered at a 10:1 effector-to-target cell ratio on Day 5 and Day 12 post-tumor implantation. Tumor volume was substantially reduced in the mice treated with the MUC1*-28zX CAR T cells.

HPAF-II pancreatic cancer cells were intravenously implanted into NSG mice. On Day 5 and Day 12 post implantation, MUC1*-28zX or untransduced T cell generated from the same donor were intravenously administered at a 10:1 effector to target cell ratio. By Day 18 the control animals had to be sacrificed due to excess tumor burden. The MUC1*-28zX treated animals showed a 4-8 fold reduction in tumor volume (FIG. 9). These demonstrate that MUC1*-28zX T cells targeting MUC1* are effective for the treatment of pancreatic cancers.

What is claimed is:

1. A chimeric antigen receptor (CAR) comprising:
   (a) a MUC1* binding single chain antibody domain comprising:
      (i) heavy chain (HC) complementarity determining regions (CDRs) comprising:
         a HC-CDR1 comprising SEQ ID NO: 18,
         a HC-CDR2 comprising SEQ ID NO: 19, and
         a HC-CDR3 comprising SEQ ID NO: 20; and
      (ii) light chain (LC) CDRs comprising:
         a LC-CDR1 comprising SEQ ID NO: 21,
         a LC-CDR2 comprising SEQ ID NO: 22, and
         a LC-CDR3 comprising SEQ ID NO: 23;
   (b) a hinge region comprising SEQ ID NO: 40;
   (c) a transmembrane domain comprising SEQ ID NO: 41; and
   (d) a signaling domain comprising SEQ ID NO: 44.

2. The CAR of claim 1, further comprising a costimulatory domain comprising SEQ ID NO: 42.

3. The CAR of claim 2, wherein the MUC1* binding single chain antibody domain comprises a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2.

4. The CAR of claim 3, wherein the linker comprises an amino acid sequence of SEQ ID NO: 24, SEQ ID NO: 26, or SEQ ID NO: 50.

5. The CAR of claim 3, wherein the linker comprises SEQ ID NO: 24.

6. The CAR of claim 3, wherein the linker comprises any one of SEQ ID NOs: 26, 28, 30, 32, 34, 36, or 38.

7. The CAR of claim 1, wherein the MUC1* binding single chain antibody domain comprises SEQ ID NO: 39.

8. The CAR of claim 1, wherein the hinge region and the transmembrane domain together comprise SEQ ID NO: 3.

9. The CAR of claim 2, wherein a cytoplasmic domain comprising the costimulatory domain and the signaling domain comprises SEQ ID NO: 4.

10. The CAR of claim 1, wherein the CAR comprises a sequence having at least 95% identity to SEQ ID NO: 48.

11. The CAR of claim 1, wherein the CAR consists of SEQ ID NO: 48.

12. An immune cell comprising the CAR of claim 1.

13. A vector comprising a nucleic acid sequence encoding the CAR of claim 1.

14. An immune cell comprising the vector of claim 13.

15. A method of treating a MUC1* positive cancer in an individual, comprising administering to the individual an engineered immune cell expressing a CAR comprising:
   (a) a MUC1* binding single chain antibody domain comprising:
      (i) heavy chain (HC) complementarity determining regions (CDRs) comprising:
         a HC-CDR1 comprising SEQ ID NO: 18,
         a HC-CDR2 comprising SEQ ID NO: 19, and
         a HC-CDR3 comprising SEQ ID NO: 20; and
      (ii) light chain (LC) CDRs comprising:
         a LC-CDR1 comprising SEQ ID NO: 21,
         a LC-CDR2 comprising SEQ ID NO: 22, and
         a LC-CDR3 comprising SEQ ID NO: 23;
   (b) a hinge region comprising SEQ ID NO: 40;
   (c) a transmembrane domain comprising SEQ ID NO: 41;
   (d) a costimulatory domain comprising SEQ ID NO: 42; and
   (e) a signaling domain comprising SEQ ID NO: 44.

16. The method of claim 15, wherein the MUC1* positive cancer comprises a solid tumor.

17. The method of claim 15, wherein the MUC1* positive cancer is breast cancer.

18. The method of claim 15, wherein the MUC1* positive cancer is lung cancer.

19. The method of claim 15, wherein the MUC1* positive cancer is pancreatic cancer.

20. The method of claim 15, wherein a section of a tumor of the MUC1* positive cancer has low MUC1* expression characterized by an anti-MUC1* H-score of 100 or less.

21. The method of claim 15, wherein a cell of the MUC1* positive cancer reacts with a MUC1* antibody in an immunohistochemistry assay.

22. The method of claim 15, wherein a cell of the MUC1* positive cancer reacts with a MUC1* antibody in an enzyme linked immunosorbent assay (ELISA).

23. The method of claim 15, wherein a cell of the MUC1* positive cancer reacts with a MUC1* antibody in flow cytometry assay.

24. The method of claim 15, wherein the method reduces tumor recurrence compared to treatment with an immune cell comprising an otherwise identical CAR wherein the signaling domain comprises SEQ ID NO: 43 instead of SEQ ID NO: 44.

25. The method of claim 15, wherein the engineered immune cell is a T cell.

26. The method of claim 25, wherein the T cell remains active after 6 or more days of stimulation with MUC1* or a synthetic MUC1* peptide comprising SEQ ID NO: 49.

27. The method of claim 25, wherein the T cell is derived from a healthy donor.

28. The method of claim 25, wherein the T cell is derived from an individual with a MUC1* positive cancer.

29. The method of claim 15, wherein the MUC1* binding single chain antibody domain comprises a heavy chain variable domain that comprises an amino acid sequence that has at least 90% identity to SEQ ID NO: 1, a linker, and a light chain variable domain that comprises an amino acid sequence that has at least 90% identity to SEQ ID NO: 2.

30. The CAR of claim 29, wherein the linker comprises an amino acid sequence of SEQ ID NO: 24, SEQ ID NO: 26, or SEQ ID NO: 50.

31. The method of claim 29, wherein the linker comprises SEQ ID NO: 24.

32. The method of claim 29, wherein the linker comprises any one of SEQ ID NOs: 26, 28, 30, 32, 34, 36, or 38.

33. The method of claim 15, wherein the MUC1* binding single chain antibody domain comprises SEQ ID NO: 39.

34. The method of claim 15, wherein the hinge region and the transmembrane domain together comprise SEQ ID NO: 3.

35. The method of claim 15, wherein a cytoplasmic domain comprising the costimulatory domain and the signaling domain comprises SEQ ID NO: 4.

36. The method of claim 15, wherein the CAR comprises a sequence having at least 95% identity to SEQ ID NO: 48.

37. The method of claim 15, wherein the CAR consists of SEQ ID NO: 48.

38. A method of killing a MUC1* positive cancer cell comprising contacting the cell with an immune cell expressing a CAR comprising:
   (a) a MUC1* binding single chain antibody domain comprising:
      (i) heavy chain (HC) complementarity determining regions (CDRs) comprising:
         a HC-CDR1 comprising SEQ ID NO: 18,
         a HC-CDR2 comprising SEQ ID NO: 19, and
         a HC-CDR3 comprising SEQ ID NO: 20, and
      (ii) light chain (LC) CDRs comprising:
         a LC-CDR1 comprising SEQ ID NO: 21,
         a LC-CDR2 comprising SEQ ID NO: 22, and
         a LC-CDR3 comprising SEQ ID NO: 23;
   (b) a hinge region comprising SEQ ID NO: 40;
   (c) a transmembrane domain comprising SEQ ID NO: 41;
   (d) a costimulatory domain comprising SEQ ID NO: 42; and
   (e) a signaling domain comprising SEQ ID NO: 44.

39. The method of claim 38, wherein the contacting is carried out in vitro.

* * * * *

SEQUENCE LISTING

```
Sequence total quantity: 50
SEQ ID NO: 1             moltype = AA  length = 121
FEATURE                  Location/Qualifiers
source                   1..121
                         mol_type = protein
                         organism = synthetic construct
SEQUENCE: 1
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYFDV WGKGTTVTVS   120
S                                                                    121

SEQ ID NO: 2             moltype = AA  length = 113
FEATURE                  Location/Qualifiers
source                   1..113
                         mol_type = protein
                         organism = synthetic construct
SEQUENCE: 2
DIVLTQSPAS LAVSPGQRAT ITCRASKSVS TSGYSYMHWY QQKPGQPPKL LIYLASNLES    60
GVPARFSGSG SGTDFTLTIN PVEANDTANY YCQHSRELPF TFGGGTKVEI KRT           113

SEQ ID NO: 3             moltype = AA  length = 42
FEATURE                  Location/Qualifiers
source                   1..42
                         mol_type = protein
                         organism = synthetic construct
SEQUENCE: 3
KHLCPSPLFP GPSKPFWVLV VVGGVLACYS LLVTVAFIIF WV                       42

SEQ ID NO: 4             moltype = AA  length = 153
FEATURE                  Location/Qualifiers
source                   1..153
                         mol_type = protein
                         organism = synthetic construct
SEQUENCE: 4
RSKRSRLLHS DYMNMTPRRP GPTRKHYQPY APPRDFAAYR SRVKFSRSAD APAYKQGQNQ    60
LYNELNLGRR EEYDVLDKRR GRDPEMGGKP RRKNPQEGLF NELQKDKMAE AFSEIGMKGE   120
RRRGKGHDGL FQGLSTATKD TFDALHMQAL PPR                                153
```

```
SEQ ID NO: 5            moltype = AA   length = 21
FEATURE                 Location/Qualifiers
source                  1..21
                        mol_type = protein
                        organism = synthetic construct
SEQUENCE: 5
MALPVTALLL PLALLLHAAR P                                              21

SEQ ID NO: 6            moltype = DNA  length = 60
FEATURE                 Location/Qualifiers
source                  1..60
                        mol_type = other DNA
                        organism = synthetic construct
SEQUENCE: 6
atgtacagga tgcagctgct gagctgcatc gccctgagcc tggccctggt gaccaacagc   60

SEQ ID NO: 7            moltype = AA   length = 20
FEATURE                 Location/Qualifiers
source                  1..20
                        mol_type = protein
                        organism = synthetic construct
SEQUENCE: 7
MYRMQLLSCI ALSLALVTNS                                                20

SEQ ID NO: 8            moltype = DNA  length = 51
FEATURE                 Location/Qualifiers
source                  1..51
                        mol_type = other DNA
                        organism = synthetic construct
SEQUENCE: 8
atgtggctgc agagcctgct gctgctgggc accgtggcct gcagcatcag c             51

SEQ ID NO: 9            moltype = AA   length = 17
FEATURE                 Location/Qualifiers
source                  1..17
                        mol_type = protein
                        organism = synthetic construct
SEQUENCE: 9
MWLQSLLLLG TVACSIS                                                   17

SEQ ID NO: 10           moltype = DNA  length = 60
FEATURE                 Location/Qualifiers
source                  1..60
                        mol_type = other DNA
                        organism = synthetic construct
SEQUENCE: 10
atggagacag acacactcct gctatgggta ctgctgctct ggttccaggt tccactggt    60

SEQ ID NO: 11           moltype = AA   length = 20
FEATURE                 Location/Qualifiers
source                  1..20
                        mol_type = protein
                        organism = synthetic construct
SEQUENCE: 11
METDTLLLWV LLLWVPGSTG                                                20

SEQ ID NO: 12           moltype = DNA  length = 66
FEATURE                 Location/Qualifiers
source                  1..66
                        mol_type = other DNA
                        organism = synthetic construct
SEQUENCE: 12
atggacatga gggtgcccgc ccagctgctg ggcctgctgc tgctgtggct gaggggcgcc   60
aggtgc                                                               66

SEQ ID NO: 13           moltype = AA   length = 22
FEATURE                 Location/Qualifiers
source                  1..22
                        mol_type = protein
                        organism = synthetic construct
SEQUENCE: 13
MDMRVPAQLL GLLLLWLRGA RC                                             22

SEQ ID NO: 14           moltype = DNA  length = 48
FEATURE                 Location/Qualifiers
source                  1..48
                        mol_type = other DNA
                        organism = synthetic construct
```

```
SEQUENCE: 14
atgcccctgc tgctgctgct gcccctgctg tgggccggcg ccctggcc                 48

SEQ ID NO: 15              moltype = AA  length = 16
FEATURE                    Location/Qualifiers
source                     1..16
                           mol_type = protein
                           organism = synthetic construct
SEQUENCE: 15
MPLLLLLPLL WAGALA                                                    16

SEQ ID NO: 16              moltype = DNA  length = 69
FEATURE                    Location/Qualifiers
source                     1..69
                           mol_type = other DNA
                           organism = synthetic construct
SEQUENCE: 16
atggacgcca tgaagagggg cctgtgctgc gtgctgctgc tgtgcggcgc cgtgttcgtg    60
agccccagc                                                            69

SEQ ID NO: 17              moltype = AA  length = 23
FEATURE                    Location/Qualifiers
source                     1..23
                           mol_type = protein
                           organism = synthetic construct
SEQUENCE: 17
MDAMKRGLCC VLLLCGAVFV SPS                                            23

SEQ ID NO: 18              moltype = AA  length = 5
FEATURE                    Location/Qualifiers
source                     1..5
                           mol_type = protein
                           organism = synthetic construct
SEQUENCE: 18
GYAMS                                                                5

SEQ ID NO: 19              moltype = AA  length = 18
FEATURE                    Location/Qualifiers
source                     1..18
                           mol_type = protein
                           organism = synthetic construct
SEQUENCE: 19
TISSGGTYIY YPDSVKGR                                                  18

SEQ ID NO: 20              moltype = AA  length = 12
FEATURE                    Location/Qualifiers
source                     1..12
                           mol_type = protein
                           organism = synthetic construct
SEQUENCE: 20
LGGDNYYEYF DV                                                        12

SEQ ID NO: 21              moltype = AA  length = 15
FEATURE                    Location/Qualifiers
source                     1..15
                           mol_type = protein
                           organism = synthetic construct
SEQUENCE: 21
RASKSVSTSG YSYMH                                                     15

SEQ ID NO: 22              moltype = AA  length = 7
FEATURE                    Location/Qualifiers
source                     1..7
                           mol_type = protein
                           organism = synthetic construct
SEQUENCE: 22
LASNLES                                                              7

SEQ ID NO: 23              moltype = AA  length = 9
FEATURE                    Location/Qualifiers
source                     1..9
                           mol_type = protein
                           organism = synthetic construct
SEQUENCE: 23
QHSRELPFT                                                            9

SEQ ID NO: 24              moltype = AA  length = 15
FEATURE                    Location/Qualifiers
source                     1..15
```

```
                       mol_type = protein
                       organism = synthetic construct
SEQUENCE: 24
GGGGSGGGGS GGGGS                                                          15

SEQ ID NO: 25          moltype = DNA  length = 60
FEATURE                Location/Qualifiers
source                 1..60
                       mol_type = other DNA
                       organism = synthetic construct
SEQUENCE: 25
ggtggcggtg gttcaggtgg tgggggctct ggcggggggtg gcagcggcgg aggagggtca        60

SEQ ID NO: 26          moltype = AA  length = 20
FEATURE                Location/Qualifiers
source                 1..20
                       mol_type = protein
                       organism = synthetic construct
SEQUENCE: 26
GGGGSGGGGS GGGGSGGGGS                                                     20

SEQ ID NO: 27          moltype = DNA  length = 75
FEATURE                Location/Qualifiers
source                 1..75
                       mol_type = other DNA
                       organism = synthetic construct
SEQUENCE: 27
ggtggcggtg gttcaggtgg tgggggctct ggcggggggtg gcagcggcgg aggagggtca        60
ggaggaggag gtagt                                                          75

SEQ ID NO: 28          moltype = AA  length = 25
FEATURE                Location/Qualifiers
source                 1..25
                       mol_type = protein
                       organism = synthetic construct
SEQUENCE: 28
GGGGSGGGGS GGGGSGGGGS GGGGS                                               25

SEQ ID NO: 29          moltype = DNA  length = 54
FEATURE                Location/Qualifiers
source                 1..54
                       mol_type = other DNA
                       organism = synthetic construct
SEQUENCE: 29
ggatctacaa gcggaagcgg caagcctggc tccggcgagg gcagcaccaa gggc               54

SEQ ID NO: 30          moltype = AA  length = 18
FEATURE                Location/Qualifiers
source                 1..18
                       mol_type = protein
                       organism = synthetic construct
SEQUENCE: 30
GSTSGSGKPG SGEGSTKG                                                       18

SEQ ID NO: 31          moltype = DNA  length = 96
FEATURE                Location/Qualifiers
source                 1..96
                       mol_type = other DNA
                       organism = synthetic construct
SEQUENCE: 31
gggggttccg gtgggggatc tggaggtggc agcggtggtg gggcggatc aggtggtggg          60
ggatcaggcg gaggcggttc aggcggcggt gggtca                                   96

SEQ ID NO: 32          moltype = AA  length = 32
FEATURE                Location/Qualifiers
source                 1..32
                       mol_type = protein
                       organism = synthetic construct
SEQUENCE: 32
GGSGGGSGGG SGGGGGSGGG GSGGGGSGGG GS                                       32

SEQ ID NO: 33          moltype = DNA  length = 54
FEATURE                Location/Qualifiers
source                 1..54
                       mol_type = other DNA
                       organism = synthetic construct
SEQUENCE: 33
ggcggcagca gcaggagcag cagcagcggc ggcggcggca gcggcggcgg cggc               54
```

```
SEQ ID NO: 34             moltype = AA   length = 18
FEATURE                   Location/Qualifiers
source                    1..18
                          mol_type = protein
                          organism = synthetic construct
SEQUENCE: 34
GGSSRSSSSG GGGSGGGG                                                      18

SEQ ID NO: 35             moltype = DNA   length = 54
FEATURE                   Location/Qualifiers
source                    1..54
                          mol_type = other DNA
                          organism = synthetic construct
SEQUENCE: 35
ggcagcacca gcggcggcgg cagcggcggc ggcagcggcg gcggcggcag cagc              54

SEQ ID NO: 36             moltype = AA   length = 18
FEATURE                   Location/Qualifiers
source                    1..18
                          mol_type = protein
                          organism = synthetic construct
SEQUENCE: 36
GSTSGGGSGG GSGGGGSS                                                      18

SEQ ID NO: 37             moltype = DNA   length = 42
FEATURE                   Location/Qualifiers
source                    1..42
                          mol_type = other DNA
                          organism = synthetic construct
SEQUENCE: 37
ggcggcagcg gcggcagcgg cggcagcggc ggcagcggcg gc                           42

SEQ ID NO: 38             moltype = AA   length = 14
FEATURE                   Location/Qualifiers
source                    1..14
                          mol_type = protein
                          organism = synthetic construct
SEQUENCE: 38
GGSGGSGGSG GSGG                                                          14

SEQ ID NO: 39             moltype = AA   length = 249
FEATURE                   Location/Qualifiers
source                    1..249
                          mol_type = protein
                          organism = synthetic construct
SEQUENCE: 39
EVQLVESGGG LVKPGGSLRL SCAASGFTFS GYAMSWVRQA PGKGLEWVST ISSGGTYIYY         60
PDSVKGRFTI SRDNAKNSLY LQMNSLRAED TAVYYCARLG GDNYYEYFDV WGKGTTVTVS        120
SGGGGSGGGG SGGGGSDIVL TQSPASLAVS PGQRATITCR ASKSVSTSGY SYMHWYQQKP        180
GQPPKLLIYL ASNLESGVPA RFSGSGSGTD FTLTINPVEA NDTANYYCQH SRELPFTFGG        240
GTKVEIKRT                                                               249

SEQ ID NO: 40             moltype = AA   length = 15
FEATURE                   Location/Qualifiers
source                    1..15
                          mol_type = protein
                          organism = synthetic construct
SEQUENCE: 40
KHLCPSPLFP GPSKP                                                         15

SEQ ID NO: 41             moltype = AA   length = 27
FEATURE                   Location/Qualifiers
source                    1..27
                          mol_type = protein
                          organism = synthetic construct
SEQUENCE: 41
FWVLVVVGGV LACYSLLVTV AFIIFWV                                            27

SEQ ID NO: 42             moltype = AA   length = 41
FEATURE                   Location/Qualifiers
source                    1..41
                          mol_type = protein
                          organism = synthetic construct
SEQUENCE: 42
RSKRSRLLHS DYMNMTPRRP GPTRKHYQPY APPRDFAAYR S                            41

SEQ ID NO: 43             moltype = AA   length = 112
FEATURE                   Location/Qualifiers
source                    1..112
```

```
                                mol_type = protein
                                organism = synthetic construct
SEQUENCE: 43
RVKFSRSADA  PAYKQGQNQL  YNELNLGRRE  EYDVLDKRRG  RDPEMGGKPR  RKNPQEGLYN   60
ELQKDKMAEA  YSEIGMKGER  RRGKGHDGLY  QGLSTATKDT  YDALHMQALP  PR          112

SEQ ID NO: 44                   moltype = AA   length = 112
FEATURE                         Location/Qualifiers
source                          1..112
                                mol_type = protein
                                organism = synthetic construct
SEQUENCE: 44
RVKFSRSADA  PAYKQGQNQL  YNELNLGRRE  EYDVLDKRRG  RDPEMGGKPR  RKNPQEGLFN   60
ELQKDKMAEA  FSEIGMKGER  RRGKGHDGLF  QGLSTATKDT  FDALHMQALP  PR          112

SEQ ID NO: 45                   moltype = AA   length = 465
FEATURE                         Location/Qualifiers
source                          1..465
                                mol_type = protein
                                organism = synthetic construct
SEQUENCE: 45
MALPVTALLL  PLALLLHAAR  PEVQLVESGG  GLVKPGGSLR  LSCAASGFTF  SGYAMSWVRQ   60
APGKGLEWVS  TISSGGTYIY  YPDSVKGRFT  ISRDNAKNSL  YLQMNSLRAE  DTAVYYCARL  120
GGDNYYEYFD  VWGKGTTVTV  SSGGGGSGGG  GSGGGGSDIV  LTQSPASLAV  SPGQRATITC  180
RASKSVSTSG  YSYMHWYQQK  PGQPPKLLIY  LASNLESGVP  ARFSGSGSGT  DFTLTINPVE  240
ANDTANYYCQ  HSRELPFTFG  GGTKVEIKRT  KHLCPSPLFP  GPSKPFWVLV  VVGGVLACYS  300
LLVTVAFIIF  WVRSKRSRLL  HSDYMNMTPR  RPGPTRKHYQ  PYAPPRDFAA  YRSRVKFSRS  360
ADAPAYKQGQ  NQLYNELNLG  RREEYDVLDK  RRGRDPEMGG  KPRRKNPQEG  LFNELQKDKM  420
AEAFSEIGMK  GERRRGKGHD  GLFQGLSTAT  KDTFDALHMQ  ALPPR                   465

SEQ ID NO: 46                   moltype = DNA   length = 597
FEATURE                         Location/Qualifiers
source                          1..597
                                mol_type = other DNA
                                organism = synthetic construct
SEQUENCE: 46
tcgacaatca  acctctggat  tacaaaattt  gtgaaagatt  gactggtatt  cttaactatg   60
ttgctccttt  tacgctatgt  ggatacgctg  ctttaatgcc  tttgtatcat  gctattgctt  120
cccgtatggc  tttcattttc  tcctccttgt  ataaatcctg  gttgctgtct  ctttatgagg  180
agttgtggcc  cgttgtcagg  caacgtggcg  tggtgtgcac  tgtctttgct  gacgcaaccc  240
ccactggttg  gggcattgcc  accacctgtc  agctcctttc  cgggactttc  gctttcccc   300
tcctattgc   acggcggaaa  tcatcgcgcc  ctgccttgc   ccgctgctgg  acaggggctc  360
ggctgttggg  cactgacaat  tccgtggtgt  tgtcgggaa   atcatcgtcc  tttccttgc   420
tgctcgcctg  tgttgccacc  tggattctgc  gcgggacgtc  cttctgctac  gtcccttcgg  480
ccctcaatcc  agcggaccttc ccttcccgcg  gcctgctgcc  ggctctgcgg  cctcttccgc  540
gtcttcgcct  tcgccctcag  acgagtcgga  tctccctttg  ggccgcctcc  ccgcctg     597

SEQ ID NO: 47                   moltype = AA   length = 493
FEATURE                         Location/Qualifiers
source                          1..493
                                mol_type = protein
                                organism = synthetic construct
SEQUENCE: 47
MALPVTALLL  PLALLLHAAR  PEVQLVESGG  GLVKPGGSLR  LSCAASGFTF  SGYAMSWVRQ   60
APGKGLEWVS  TISSGGTYIY  YPDSVKGRFT  ISRDNAKNSL  YLQMNSLRAE  DTAVYYCARL  120
GGDNYYEYFD  VWGKGTTVTV  SSGGGGSGGG  GSGGGGSDIV  LTQSPASLAV  SPGQRATITC  180
RASKSVSTSG  YSYMHWYQQK  PGQPPKLLIY  LASNLESGVP  ARFSGSGSGT  DFTLTINPVE  240
ANDTANYYCQ  HSRELPFTFG  GGTKVEIKRT  TTTPAPRPPT  PAPTIASQPL  SLRPEACRPA  300
AGGAVHTRGL  DFACDIYIWA  PLAGTCGVLL  LSLVITLYCK  RGRKKLLYIF  KQPFMRPVQT  360
TQEEDGCSCR  FPEEEEGGCE  LRVKFSRSAD  APAYKQGQNQ  LYNELNLGRR  EEYDVLDKRR  420
GRDPEMGGKP  RRKNPQEGLY  NELQKDKMAE  AYSEIGMKGE  RRRGKGHDGL  YQGLSTATKD  480
TYDALHMQAL  PPR                                                         493

SEQ ID NO: 48                   moltype = AA   length = 444
FEATURE                         Location/Qualifiers
source                          1..444
                                mol_type = protein
                                organism = synthetic construct
SEQUENCE: 48
EVQLVESGGG  LVKPGGSLRL  SCAASGFTFS  GYAMSWVRQA  PGKGLEWVST  ISSGGTYIYY   60
PDSVKGRFTI  SRDNAKNSLY  LQMNSLRAED  TAVYYCARLG  GDNYYEYFDV  WGKGTTVTVS  120
SGGGGSGGGG  SGGGGSDIVL  TQSPASLAVS  PGQRATITCR  ASKSVSTSGY  SYMHWYQQKP  180
GQPPKLLIYL  ASNLESGVPA  RFSGSGSGTD  FTLTINPVEA  NDTANYYCQH  SRELPFTFGG  240
GTKVEIKRTK  HLCPSPLFPG  PSKPFWVLVV  GGVLACYSL   LVTVAFIIFW  VRSKRSRLLH  300
SDYMNMTPRR  PGPTRKHYQP  YAPPRDFAAY  RSRVKFSRSA  DAPAYKQGQN  QLYNELNLGR  360
REEYDVLDKR  RGRDPEMGGK  PRRKNPQEGL  FNELQKDKMA  EAFSEIGMKG  ERRRGKGHDG  420
LFQGLSTATK  DTFDALHMQA  LPPR                                            444

SEQ ID NO: 49                   moltype = AA   length = 45
```

```
FEATURE              Location/Qualifiers
source               1..45
                     mol_type = protein
                     organism = synthetic construct
SEQUENCE: 49
GTINVHDVET QFNQYKTEAA SRYNLTISDV SVSDVPFPFS AQSGA                      45

SEQ ID NO: 50        moltype = AA  length = 25
FEATURE              Location/Qualifiers
source               1..25
                     mol_type = protein
                     organism = synthetic construct
VARIANT              1..25
                     note = This sequence may encompass 1-5 GGGGS repeating units
SEQUENCE: 50
GGGGSGGGGS GGGGSGGGGS GGGGS                                            25
```